US007534368B2

(12) United States Patent
    Martin

(10) Patent No.: US 7,534,368 B2
(45) Date of Patent: *May 19, 2009

(54) OXIDIZING COMPOSITION INCLUDING A GEL LAYER

(75) Inventor: Roy W. Martin, Downers Grove, IL (US)

(73) Assignee: Truox, Inc., McClellan, CA (US)

( * ) Notice: Subject to any disclaimer, the term of this patent is extended or adjusted under 35 U.S.C. 154(b) by 659 days.

This patent is subject to a terminal disclaimer.

(21) Appl. No.: 11/253,977

(22) Filed: Oct. 18, 2005

(65) Prior Publication Data

US 2006/0197058 A1    Sep. 7, 2006

Related U.S. Application Data

(63) Continuation-in-part of application No. 11/154,086, filed on Jun. 15, 2005, which is a continuation-in-part of application No. 11/070,132, filed on Mar. 1, 2005.

(51) Int. Cl.
    *C01B 11/10*     (2006.01)
    *C01B 11/02*     (2006.01)
    *C11D 3/395*     (2006.01)

(52) U.S. Cl. .......................... 252/187.23; 252/187.21; 252/187.33; 252/187.34; 252/186.25

(58) Field of Classification Search ............ 252/187.21, 252/187.23
    See application file for complete search history.

(56) References Cited

U.S. PATENT DOCUMENTS

| 3,873,685 | A |   | 3/1975  | Kibbel, Jr. et al. ............ 424/16 |
| 4,800,082 | A |   | 1/1989  | Karbowski et al. .......... 424/409 |
| 5,178,787 | A |   | 1/1993  | Hung et al. .................... 252/90 |
| 5,464,636 | A |   | 11/1995 | Hight et al. .................. 424/661 |
| 5,603,941 | A |   | 2/1997  | Farina et al. ................. 424/405 |
| 5,783,540 | A |   | 7/1998  | Secemski et al. ............ 510/224 |
| 5,962,387 | A |   | 10/1999 | Gorlin et al. ................. 510/224 |
| 5,965,264 | A | * | 10/1999 | Barenberg et al. .......... 428/402 |
| 6,238,643 | B1| * | 5/2001  | Thangaraj et al. ............ 423/477 |
| 6,251,848 | B1|   | 6/2001  | Holderbaum et al. ....... 510/446 |
| 6,277,408 | B1| * | 8/2001  | Wellinghoff et al. ........ 424/473 |
| 6,319,888 | B2|   | 11/2001 | Wei et al. ..................... 510/441 |
| 6,384,006 | B1|   | 5/2002  | Wei et al. ..................... 510/376 |
| 6,569,353 | B1|   | 5/2003  | Giletto et al. ........... 252/186.28 |
| 6,699,404 | B2|   | 3/2004  | Speronello et al. ..... 252/187.23 |
| 6,863,830 | B1|   | 3/2005  | Purdy et al. .................. 210/756 |
| 6,899,840 | B2|   | 5/2005  | Ueda et al. .................... 264/145 |
| 7,204,931 | B2| * | 4/2007  | Martin et al. ................ 210/755 |
| 7,465,410 | B2| * | 12/2008 | Martin et al. .......... 252/186.25 |
| 2001/0012504 | A1|   | 8/2001  | Thangaraj et al. ........... 423/477 |
| 2002/0155067 | A1| * | 10/2002 | MacGregor ................... 424/44 |
| 2003/0080317 | A1| * | 5/2003  | Speronello et al. .......... 252/175 |
| 2005/0155936 | A1| * | 7/2005  | Martin et al. ................ 210/754 |

* cited by examiner

*Primary Examiner*—Joseph D Anthony

(57) ABSTRACT

A composition that generates a target product and releases a biocidal solution containing the target product is presented. The composition comprises reactants capable of generating the target product through a chemical reaction, a halogen, and a gel-forming material. The chemical reaction is triggered when the reactants are contacted by a main solvent (e.g., water). The gel-forming material makes the composition stable for storage. Upon being exposed to the main solvent, the gel-forming material forms a gelatinous structure that creates a chamber within the composition enclosing some of the reactants such that the target product is generated in the chamber. The gelatinous structure contributes to the high yield of the target product (e.g., chlorine dioxide) and its controlled release. The halogen (e.g., bromine and/or chlorine) enhances the biocidal effect of the target product.

35 Claims, 14 Drawing Sheets

US 7,534,368 B2

OXIDIZING COMPOSITION INCLUDING A GEL LAYER

RELATED APPLICATIONS

This application is a Continuation-in-Part (CIP) of U.S. patent application Ser. No. 11/154,086 filed on Jun. 15, 2005, which is in turn a CIP of U.S. patent application Ser. No. 11/070,132 filed on Mar. 1, 2005 now abandoned. The contents of both patent applications are incorporated by reference herein.

FIELD OF INVENTION

This invention relates generally to an oxidizing compound and more particularly to a biocidal oxidizing compound that is stabilized for storage.

BACKGROUND

Oxidizers are commonly used to effectively destroy organic and inorganic contaminants. Some of the typical applications of oxidizers include treatment of water systems and inactivation of bacteria and viruses in various media.

Although oxidizers are used in numerous applications, there are also applications where they are not used even though their utility is well established. The reason these oxidizers are not used often relates to their instability during storage. Oxidizers such as hypochlorous acid, peracids, and chlorine dioxide, for example, could be used in more applications than the disinfection applications that they are already used in if their stability can be improved. The problem with some of these powerful oxidizers such as hypochlorous acid and peracids is that their activity level tends to decrease during storage. Since the effectiveness of the oxidizers in various applications depends on their concentrations, activity levels, and the level of demand on the oxidizer as measured by its oxidation reduction potential (ORP), a reduction in the activity level of the oxidizers impedes their performance in the various applications. Thus, even if an oxidizer is initially highly effective, the effectiveness decreases during storage.

A few methods are currently used to get around this storage problem. One of these methods, which is the point-of-use generation method or the in-situ method, is desirable because it eliminates the need for prolonged storage. However, on a practical level, these point-of-use generation methods are not widely employed because they require expensive equipment and specialized expertise. Other in-situ generation methods involve adding the reagents to the water to produce the target product. However, when doing this, significant dilution of reagents as well as competing reactions impede the level of conversion to the target product.

Sometimes, the reagents are coated to provide a protective shield or barrier between the reagents and the environmental elements, thereby making the reagents easier to store and use in formulations. The protective coatings are designed so that when they are combined with water, they dissolve and rapidly release the reagents. Silicates, for example, are widely used in laundry detergent applications. In the alkaline condition induced by the laundry formulation, the silicate coating rapidly dissociates and releases the encased additives into the bulk water. There are also instances where a highly hydrophobic coating such as a wax or slow-dissolving coating is used for time-release purposes. These cases operate on the basis of a mechanism similar to the mechanism of the silicate coating in that the outer coating material quickly dissolves to expose the enclosed material to the solvent in the environment.

Various compositions have been made to enhance the bleaching/oxidizing performance in an application. Such enhancement is desirable because the generally effective hydrogen peroxide donors such as percarbonate, perborate, and persulfate-based additives do not remove stubborn stains from clothing. To enhance their bleaching ability under the conditions that are typical to the application (e.g., laundry water), precursors are added to induce formation of a more effective bleaching agents (e.g., tetraacetyl-ethylenediamine (TAED)) in-situ. However, this addition of bleaching agent precursors has its disadvantages. For example, high concentrations of additives are needed to achieve effective results, increasing both the cost and inconvenience.

Another way of enhancing peroxygen compounds' performance is to make them more stable, thus allowing long-term storage. Sometimes, the peroxygen compounds and the formulations they are used in are coated to enhance storage stability. These coatings, however, do not always dissolve quickly and therefore increase the time it takes for the peroxygen compound to become effective. One of the ways to allow long-term storage of oxidizers such as potassium monopersulfate and chlorine is to store them in packages or bags. The packages or bags are designed to dissolve in water, so that they can be directly thrown into a body of water. Although the use of bags provides for easy application in large scale or macro applications, their utility is limited in that they can be used only for applications of a certain scale.

U.S. Pat. No. 6,699,404 to Speronello ("the Speronello patent") discloses a massive body having a porous structure which substantially increases the percent conversion of chlorite to chlorine dioxide when compared to chlorite powder. The Speronello patent discloses two types of massive bodies: a water soluble type and a substantially water insoluble type. The substantially water insoluble massive body forms a porous framework that provides a higher efficiency of the conversion compared to the water-soluble massive body. According to the test data provided in the Speronello patent the maximum concentration of chlorine dioxide produced by a massive body that forms the porous framework is 149.4 mg/L. The water-soluble massive body reported (example 4) a maximum 27.4 mg/L.

In order to achieve 70% or more conversion of the chlorite to chlorine dioxide using the method disclosed in the Speronello patent, a substantial amount of inert materials are added to produce the porous structure or the porous framework. The level of inert salts ranges from 18 wt. % to 80 wt. %, with higher weight percentages increasing the conversion efficiency. The high levels of inert material, particularly in the water-soluble massive body, are further illustrated in commercial practice. For example, Aseptrol®, which is the commercialized product embodying the invention disclosed in the Speronello patent, is a water soluble tablet that requires 1.5 grams of Aseptrol® to 1 liter of water to produce 100 mg/L chlorine dioxide. This equates to approximately 67 mg/L chlorine dioxide based on 1 gram tablet per liter. The weight-% yield, which is defined as weight chlorine dioxide per weight of tablet, is low because of the high level of inert material. According to the data reported in the Speronello patent, the weight % yield is less than 15 wt. %, and less than 3% in the case of the water-soluble massive body. Based on the commercial product Aseptrol®, the weight percent yield of the water soluble commercial product is 6.7 wt. %.

It is desirable to increase the concentration of chlorine dioxide produced by a given mass of tablet to improve the economics based on the cost per pound of the tablet material versus pounds of chlorine dioxide produced. Such increase would also result in an overall performance enhancement offered by higher concentrations of chlorine dioxide. To achieve this objective, tablet conversion efficiency of >70% and a high reactant weight percent are desirable. It is also desirable to substantially increase the concentration of chlorine dioxide using a completely water-soluble composition to eliminate the problems associated with water insoluble constituents or byproducts such as residue silica based clays, or mineral salts such as calcium sulfate.

U.S. Pat. Nos. 6,384,006 and 6,319,888 to Wei et al. ("the Wei patents") disclose a system for forming and releasing an aqueous peracid solution. The system includes a container and a peracid forming composition that includes about 10-60 wt. % of a chemical heater that, upon contact with water, generates heat to increase the yield of the peracid.

The Wei patents describe the potential use of a viscosity modifier within a permeable container to increase the viscosity in the localized area from about 300 to about 2,000 centipoise. The increased viscosity restricts and slows down the movement of peracid precursor and/or peroxygen source out of the permeable container. This results in an increased residence time of the peracid precursor and peroxygen source within the permeable container, which in turn translates to a greater reaction rate.

U.S. Pat. No. 6,569,353 to Giletto et al. ("the Giletto patent") discloses using silica gel to increase the viscosity of various oxidants including an in-situ generated oxidant in order to keep them in intimate contact with the agents targeted for oxidation.

U.S. Published Application No. 2001/0012504 to Thangaraj et al. ("the Thangaraj application") discloses a composition for producing chlorine dioxide comprising an acid source and a chlorite source, and a method comprising enclosing the composition in a gelatin capsule or membrane sheet such as a "tea bag".

In order to improve reaction kinetics, the above references teach using substantial quantities of inert materials to either provide a porous structure as in the case of the Speronello patent, or heat as in the cases of the Wei patents. While viscosity modifiers are referenced in the Wei patents, the viscosity range disclosed in the Wei patents does not reflect the formation of a gel.

Search still continues for a method of stabilizing reactive components for storage without compromising or limiting their function during usage.

SUMMARY

In one aspect, the invention is a composition that generates a target product and releases a biocidal solution containing the target product. The composition comprises reactants capable of generating the target product through a chemical reaction, a halogen that is capable of synergistically providing a biocidal effect with the target product, and a gel-forming material. The chemical reaction is triggered when the reactants are contacted by a main solvent. The reactants include a free halogen donor that makes up about 40-90 weight % of the composition and a chlorite donor that makes up about 9-50 weight % of the composition. The gel-forming material, which is in contact with the reactants, makes up about 0.1 to 10 weight % of the composition. Upon being exposed to the main solvent, the gel-forming material forms a gelatinous structure that creates a chamber within the composition enclosing some of the reactants such that the target product is generated in the chamber, wherein the gelatinous structure restricts diffusion of the reactants and the target product out of the chamber, restricts the diffusion of the main solvent into the chamber, and wherein the gelatinous structure dissipates when a depletion level is reached inside the chamber. Different parts of the composition are exposed to the main solvent at different times.

In another aspect, the invention is a method of producing a composition that generates a target product and releases a biocidal solution containing the target product. The method entails forming an agglomerate of reactants that produce an in-situ generated oxidizer including at least one of chlorine dioxide and hypobromite, and coating the agglomerate of reactants with a slow-dissolving free halogen donor.

DETAILED DESCRIPTION OF THE EMBODIMENT(S)

Figure 1:
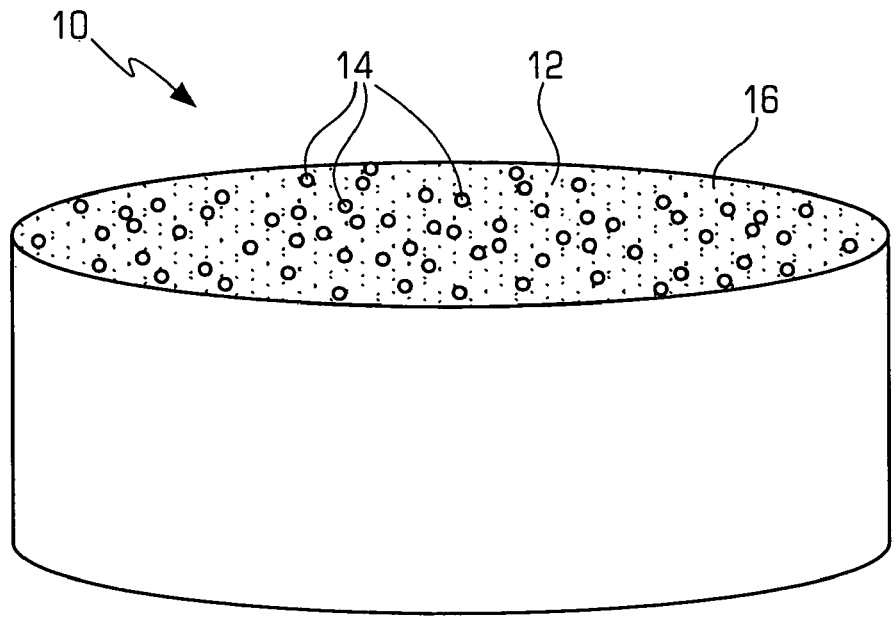
FIG. 1 is an exemplary embodiment of reactor in accordance with the invention.

The invention is particularly applicable to generation and release of oxidizers that have bleaching, biocidal, or virucidal properties and it is in this context that the invention will be described. It will be appreciated, however, that the reactor, the method of making the reactor, and the method of using the reactor in accordance with the invention has greater utility and may be used for any other target product(s). Although the main solvent is described as water for clarity of illustration, the invention is not so limited.

"Reaction chamber" is a space that is defined by the outline of a colloidal gel wall, and includes the enclosed by the colloidal gel, the colloidal gel itself, and any pores or channels in the colloidal gel. A "main solvent," is any solvent that dissolves the reactant(s) and triggers a chemical reaction. A "polymer," as used herein, includes a copolymer. A substance that is transported at a "controlled rate" does not cross a physical boundary explosively all at once but gradually, over a desired period of time.

As used herein, "depletion level" indicates a predetermined concentration level of the reactant(s) and the target product in a reaction chamber. When a reaction chamber is contacted by the main solvent, a chemical reaction is triggered and the reactant(s) in the reaction chamber are converted to the desired target product. The target product then leaves the reactor chamber at a controlled rate. The depletion level may be defined by parameters other than reactant concentration that also indicate the rate of target product generation, such as the pH level or the concentrations of the target product or a byproduct.

When the reactor wall "disintegrates," it could collapse due to a pressure difference between the inside and the outside of the reactor, dissolve in the main solvent, or come apart and dissipate due to forces applied by the movement in the main solvent. A membrane is a porous material that allows permeation of the solvent and diffusion of the product. "Water," as used herein, is not limited to pure water but can be an aqueous solution. A gelatinous structure "dissipates" by dissolving or dispersing in the main solvent.

"Gel," "hydro-gel," and its various derivations (i.e. gelatinous) describes a material or composition of materials that undergo a high degree of cross-linking or association when hydrated and dispersed in the dispersing medium, or when dissolved in the dispersing medium. This cross-linking or association of the dispersed phase will alter the viscosity of the dispersing medium to a level which restricts the movement of the dispersing medium. As used herein, "suspension" refers to a two-phase system consisting of a finely divided solid dispersed (suspended) in a liquid (the dispersing medium). Gels contain suspended particles but are different from suspensions in that these suspended particles create a three-dimensional structure of interlacing particles or solvated macromolecules that restrict the movement of the dispersing medium.

A "gel-forming material" is comprised of at least a polymer that, upon contact with a hydrophilic solvent, produces a hydrocolloid or hydro-gel. The polymer can be natural, such as a gum (i.e. Xanthun gum), semisynthetic such as a polysaccharide (i.e. cellulose derivative), or synthetic such as a poloxamer or carbomer.

"Composite gel" and "sol-gel" describe a gel that has increased rigidity due to the presence of a secondary component that stiffens the gel, thereby producing a gel with a viscosity substantially higher than that obtained using the gel-forming material alone while at the same pH and temperature. A composite gel includes those gels defined as "sol-gel" which is comprised of a colloidal solution suspended in a gel.

A "stiffening agent" can be water-soluble or substantially water-insoluble. When combined with a gel-forming material, the stiffening agent substantially increases the viscosity of the gel-structure to a level where the gel increases its rigidity to where the gel-structure restricts the movement or dispersion of the gel and the dispersing medium (i.e. water or solvent).

A "gelatinous structure" comprises the three-dimensional hydrocolloid or hydro-gel produced by the hydrolysis of the gelling agent, which may include at least one natural, semi-synthetic, and synthetic hydrocolloid forming polymer, as well as any reactants or products restrained or trapped by the three-dimensional gel. The gelatinous structure describes a region defined by the coalesced gelatinous composition which forms the 3-dimensional structure. The regional boundaries are generally defined by the innermost portion of the gelatinous composition (approaching the center of the agglomerate) to the outermost boundary of the gelatinous composition (interfacing with the bulk of the dispersing medium). The gelatinous structure may have both pseudoplastic and thixotropic properties, and achieve a viscosity gradient across the region.

A "gelling agent" defines the set of components required to produce the gelatinous structure. This includes at least the gel-forming material, and can include the stiffening agents, effervescing agents, pH buffers, etc. if and when the application requires.

A "granule" is an agglomerate of reactant(s) typically having a particle size less than 1 mm. When a granule is coated with a gel-forming material, each coated granule functions as an independent reactor. The granules may be coated with a fluidized bed drier and an atomized spray. However, granules may also be coated with a powder of an additive, then combined with other components such as a free halogen donor before being agglomerated again.

If the gel contains small discrete particles, the gel is called a "two-phase system." Two-phase systems are thixotropic, i.e., they are semisolid on standing but liquefy when shaken. Two-phase systems are formed when substantially water-insoluble additives are combined with the gel-forming material. If the particle size in a two-phase system is large, the gel is referred to as a magma. Examples of two-phase systems include aluminum hydroxide gel and bentonite magma.

"Single-phase system" If the gel does not appear to have discrete particles, it is called as a one-phase system. Single-phase systems contain linear or branched polymer macromolecules that dissolve in water and have no apparent boundary with the dispensing medium. These macromolecules are classified as natural polymers.

"Thixotropic" indicates the property exhibited by certain gels of becoming fluid when stirred or shaken and returning to the semisolid state upon standing.

"Pseudoplastic" indicates the property exhibited by gels where the gel retains a high viscosity at low shear rates (during storage) and low viscosity at high shear rates (during shaking, pouring, or spreading).

To maximize the yield in a chemical reaction, it is usually preferable to start with high concentrations of reactants because the molar concentrations of the reactants determine the rate of reaction and the subsequent product yield. Therefore, adding reactants to a large body of water to be treated is not an effective way to generate the desired product in-situ. Adding the reactants to the water lowers the reactant concentrations, and the resulting conversion of the reactants to the desired product(s) is generally poor. Another factor to be considered is the side reactions. When generating an agent in-situ, the oxidizer reactant is often consumed in reactions other than those desired for the in-situ production of the target product. Therefore, adding the reactants to the water to be treated results in more reagent requirements, longer reaction time, and/or an overall decreased yield of the target product.

Furthermore, the chemical environment, such as pH, can adversely affect the in-situ production of the target product. For example, reactions that are acid catalyzed are not supported in alkaline conditions such as laundry wash water. By isolating the reactants and controlling the conditions inside the reactor, efficient generation of the target product(s) occurs regardless of the conditions external to the reactor.

When an oxidizer, such as potassium monopersulfate (PMPS), is added to water to convert sodium chloride to hypochlorous acid through a hypohalite reaction, the conversion or yield is dependent on the molar concentrations of the reactants. As described above, however, adding a given amount of reactants to a large volume of water yields poor conversion to the target product. Furthermore, potassium monopersulfate is highly reactive with organic chemical oxygen demand (COD). Thus, upon being exposed to the bulk solution, the PMPS reacts with the COD and further reduces the concentration of PMPS that is available to induce the hypohalite reaction.

The invention is based on the concept that a high yield can be maintained by controlling the rate at which the reactants are exposed to water. More specifically, if the reactants were first exposed to a small volume of water and allowed to react to generate the target product, a high yield of the target product can be obtained because the reactant concentrations will be high. Then, the target product can be exposed to a larger volume of water without compromising the yield. The rate at which the reactants are exposed to water has to be such that the target product is generated in high-yield before more water dilutes the reactants. The invention controls the reactants' exposure to water by coating the reactants with a material that allows water to seep in and reach the reactants at a controlled rate.

The invention is also based on the fact that chlorine dioxide makes an effective biocide with advantages over other common oxidizing biocides. Chlorine dioxide, when combined with other halogen biocides, provides a synergistic effect that increases the inactivation rate of organisms at a higher rate than either biocide fed alone.

However, thus far, the oxidizing power of chlorine dioxide has not been fully exploited because the cost of equipment to produce chlorine dioxide in-situ to the application is prohibitively high. Also, when using conventional powders or tablets, the economics are severely compromised due to poor "weight % yield" of the powders and tablets as well as the cost of producing these chlorine dioxide generators. The poor "weight % yield" is demonstrated in the '404 Patent discussed above.

Depending on the embodiment, the invention may be a reactor that is stable enough for storage and useful for generating high yields of products in-situ, product including oxidizers, biocides, and/or virucidal agents. A "soluble" reactor has walls that dissolve in the main solvent after the reaction has progressed beyond a certain point (e.g, the depletion level has been reached). The soluble reactor is stable when dry. When mixed with a main solvent (e.g., water), however, the coating material that forms the outer wall of the soluble reactor allows the solvent to slowly seep into the reactor space, dissolve the reactant(s), and trigger a chemical reaction. The chemical reaction generates a target product. Since the concentrations of the reactants are high within the soluble reactor, a high yield of the target product is achieved inside the reactor. After the reactor space reaches the predetermined depletion level, the coating material disintegrates.

In some embodiments, the reactor of the invention is a "micro-reactor" having a diameter or width in the range of 10-2000 μm. However, the reactor is not limited to any size range. For example, the reactor may be large enough to be referred to as a pouch. A single reactor may be both a micro-reactor and a soluble reactor at the same time. Furthermore, a reactor may have a soluble wall and a non-soluble wall.

Reactants

Reactants are selected to induce the formation of the desired product(s). When determining the ratio of reactants, consideration should be given to the desired ratio of products. Single species generation of agent is achieved with proper optimization of reagent ratios.

High conversion of reactants and good stability of products are achieved by adding stabilizers and/or pH buffering agents to the mixture of reactants. For example, to produce N-haloimides such as N-chlorosuccinimide, N-succinimide is added to a mixture containing PMPS and NaCl. Also, an organic acid (e.g., succinic acid) and/or inorganic acids (e.g., monosodium phosphate) may be applied to ensure that the pH of the reactant solution is within the desired range for maximum conversion to the haloimide.

The reaction chambers 20 contain reactants that, upon dissolution to form a liquid phase, induce the in-situ generation of the desired target product(s). For example, where the desired target product is a bleaching/oxidation agent, the reactant may be a peroxygen compound such as a persulfate, inorganic peroxide, alkyl peroxide, and aryl peroxide, or a free halogen such as dichloroisocyanuric acid, a salt of dichloroisocyanuric acid, a hydrated salt of dichloroisocyanuric acid, trichlorocyanuric acid, a salt of hypochlorous acid, bromochlorodimethylhydantoin and dibromodimethylhydantoin.

1) Dioxirane

Where the target product is dioxirane, the oxidizer reactant may be one of potassium persulfate, sodium persulfate, ammonium persulfate, potassium monopersulfate, permanganate, and a Caro's acid precursor. The Caro's acid precursor is a combination of a peroxide donor (e.g., urea peroxide, calcium peroxide, magnesium peroxide, sodium peroxide, potassium peroxide, perborate, perphosphate, persilicate, and percarbonate) and a sulfuric acid donor (e.g., sodium bisulfate and pyrosulfate and a sulfuric acid donor). In addition to the oxidizer reactant, the reactant 10 may also include an organic compound containing carbonyl groups (C=O) to produce dioxirane. Preferably, the organic compound has 3-20 carbons. The reactant composition may be 10-80 wt. % oxidant and 0.5-50 wt. % carbonyl donor such as aldehydes, ketones, and carboxylic acids. If a pH buffer is used, it does not exceed 30 wt. % of the pH buffer. Dioxirane formation is typically most efficient around neutral pH.

In another embodiment, the reactants may include a peroxygen donor, a carbonyl donor, and an optional alkaline pH buffer. The peroxygen compound may be, for example, potassium monopersulfate. The carbonyl donor may be an alkyl, aryl, or alkyl-aryl ketone or aldehyde. If the alkaline pH buffer is used, it may be a mineral salt of phosphate, bicarbonate, carbonate, hydroxide, or silicate. Where the alkaline pH buffer is not incorporated into the composition, it may be supplied by being mixed with the main solvent.

2) Percarboxylic Acid

Where the target product is a peroxycarboxylic acid (also referred to as percarboxylic acid), the reactants may include an oxidizer reactant such as a peroxide donor (e.g., urea peroxide, calcium peroxide, magnesium peroxide, sodium peroxide, lithium peroxide, potassium peroxide), sodium percarbonate, sodium perborate, persulfate(s), monopersulfate, persilicate, perphosphate, or permanganate. The reactants may also include a carboxylic acid donor such as an ester or acetic acid in the form of an anhydride (e.g., acetic anhydride). Another example is inclusion of tetraacetyl-ethylenediamine (TAED) with the peroxide donor for production of peracid in alkaline conditions. The overall reactant composition is about 10-80 wt. % oxidizer reactant and about 1-40 wt. % carboxyl group donor. Optionally, a filler and/or a pH buffer may be mixed with the reactants and the binder. The molar ratios are optimized and pH buffers may be added to the reactants. Upon dilution with water, the reactants dissolve and produce peracetic acid in high yield.

3) Hypohalite

Where the target product is a hypohalite, the reactants may include potassium persulfate, sodium persulfate, ammonium persulfate, potassium monopersulfate, permanganate, or a Caro's acid precursor. The Caro's acid precursor is a combination of a peroxide donor (urea peroxide, calcium peroxide, magnesium peroxide, sodium peroxide, potassium peroxide, perborate, perphosphate, persilicate, and percarbonate) and a sulfuric acid donor (sodium bisulfate and pyrosulfate). The reactants incude about 10-80 wt. % oxidizer reactant and about 0.5-40 wt. % halogen donor. Optionally, a binder, a filler, and a pH buffer may be added to the reactants.

In one embodiment where the product is a hypo-bromite and its various equilibrium derivatives (hypobromous acid), the reactants may include a free halogen donor (e.g., dichloroisocyanuric acid, trichloroisocyanuric acid) and an inorganic bromide.

4N-halo-amide

Where the target product is an N-halo-amide, the reactant may be a potassium persulfate, sodium persulfate, ammonium persulfate, potassium monopersulfate, permanganate, or a Caro's acid precursor. The reactants may also include a monovalent metal salt, a divalent metal salt, or a trivalent metal salt, as well as an N-hydrogen donor capable of reacting with hypo-halite to generate the target product and a chlorite donor. The composition of the reactants is about 10-80 wt. % oxidizing reactant, 0.5-40 wt. % a halogen donor, and 2-50 wt. % stabilizer. Optionally, a binder, a filler, and a pH buffer may be added to the reactants.

In another embodiment, the reactants may include a peroxygen donor, a halogen donor, and an N-amide donor (e.g., N-succinimide). The peroxygen donor may be potassium monopersulfate.

5) Chlorine Dioxide

Where the target product is chlorine dioxide, the reactor composition is about 10-80 wt. % acid source, about 0.5-20 wt. % halogen donor (also referred to as a free halogen source), and about 0.5-15 wt. % chlorite donor. In one embodiment, the acid source may be potassium persulfate, sodium persulfate, ammonium persulfate, potassium monopersulfate, permanganate, or a Caro's acid precursor. The acid source may be inorganic or organic. The halogen donor may be, for example, magnesium chloride, calcium chloride, sodium chloride, or potassium chloride. The chlorite donor may be sodium chlorite potassium chlorite, magnesium chlorite, or calcium chlorite, or various combinations thereof.

In another variation where the product is chlorine dioxide, the composition is about 10-60 wt. % oxidizing reactant (e.g., an acid source), about 0.5-40 wt. % free halogen donor, and about 1-50 wt. % metal chlorite. The reactant may be potassium monopersulfate, a metal bisulfate (e.g., sodium bisulfate), a metal pyrosulfate, or a metal phosphate. The halogen donor may be sodium chloride, calcium chloride, magnesium chloride, potassium chloride, dichloroisocyanuric acid, a salt of dichloroisocyanuric acid (e.g., a sodium salt thereof), a hydrated salt of dichloroisocyanuric acid, trichlorocyanuric acid, a salt of hypochlorous acid, bromochlorodimethylhydantoin, or dibromodimethylhydantoin. A sodium salt of dichloroisocyanuric acid dihydrate may also be used. The chlorite may be a mono- or di-valent chlorite such as sodium or calcium chlorite. Trichloroisocyanuric acid may also serve dual function as both the acid source and the free halogen source.

Another example of a chlorine dioxide generator contains sodium chlorite, sodium bisulfate, calcium/magnesium chloride, and the sodium salt of dichloroisocyanuric acid dihydrate. Free halogen donor is optionally incorporated into the reactor 10.

Yet another embodiment of the chlorine dioxide generator includes a peroxygen source and a chlorite source as the reactants. Free halogen source and an acid source may be added if desired.

Yet another embodiment of the chlorine dioxide generator includes TCCA (trichloroisocyanuric acid) and a chlorite donor, preferably sodium chlorite. In this case, the TCCA acts as both a free halogen donor and an acid source. Ratios can range from 50-99 wt. % TCCA and 1-50 wt. % sodium chlorite.

Where the reactants include a metal chlorite, an acid source, and a free halogen donor, the chemical reaction that occurs when the main solvent reaches the reactants generates an oxidizing solution containing chlorine dioxide and free halogen. The concentration of the free halogen in the oxidizing solution is less than ½ of the chlorine dioxide concentration in the oxidizing solution, preferably less than ¼ of the chlorine dioxide concentration in the oxidizing solution, and more preferably less than ¹/₁₀ of the chlorine dioxide concentration in the oxidizing solution. The ratio of the chlorine dioxide concentration to the sum of the chlorine dioxide concentration and chlorite anion concentration in such solution is at least 0.25:1, preferably at least 0.6:1, and more preferably at least 0.75:1 by weight. In some embodiments with a high free halogen content, the free halogen concentration in the oxidizing solution may be as high as 100 times the chlorine dioxide concentration. The ratio of the chlorine dioxide concentration to the sum of the chlorine dioxide concentration and chlorite anion concentration in such solution is at least 0.5:1 by weight.

In another embodiment, the reactant is urea peroxide, calcium peroxide, magnesium peroxide, sodium percarbonate sodium perborate, persulfate(s), monopersulfate, persilicate, perphosphate, sodium, lithium, or potassium peroxide. A halogen donor and a chlorate donor such as sodium chlorate, potassium chlorate, lithium chlorate, magnesium chlorate, and calcium chlorate may be included.

In yet another embodiment, the composition includes a free halogen donor that makes up about 14-22 wt. % of the composition (25-35 wt% dichloroisocyanuric acid), 25-35 wt. % sodium bisulfate, and 30-40 wt. % sodium chlorite. In accordance with the invention, at least 70% of the sodium chlorite is converted to chlorine dioxide upon the agglomerate composition's contacting water.

6) Hydroxyl Radical

Where the target product is a hydroxyl radical, the reactant composition may be about 10-80 wt. % reactants (e.g., peroxide donor and an acid source), about 0.001-10 wt. % a transition metal, and about 1-30 wt. % pH buffer. In addition, a binder and a filler may be used. The reactants may be urea peroxide, calcium peroxide, magnesium peroxide, sodium percarbonate sodium perborate, persulfate(s), monopersulfate, persilicate, perphosphate, sodium, lithium, permanganate, or potassium peroxide. The transition metal is a chelating agent selected from a group consisting of trisodium pyrophosphate, tetrasodium diphosphate, sodium hexametaphosphate, sodium trimetaphosphate, sodium tripolyphosphate, potassium tripolyphosphate, phosphonic acid, di-phosphonic acid compound, tri-phosphonic acid compound, a salt of a phosphonic acid compound, ethylene diamine-tetra-acetic acid, gluconate, or another ligand-forming compound.

Hydroxyl radical may be produced with a reactor that contains a metal catalyst. The metal catalyst may be mixed with the reactants, coated on the binder layer, or included in the reactor wall, for example in the pores on the membrane. The metal catalyst may be Cu (II), Mn (II), Co (II), Fe (II), Fe (III), Ni (II), Ti (IV), Mo (V), Mo (VI), W (VI), Ru (III), or Ru (IV). Upon dilution with water the composition releases peroxide. Under neutral to acidic conditions is converted to hydroxyl radicals upon reaction with the catalyst. The catalyst remains unaltered.

7) Singlet Oxygen

Where the target product is a singlet oxygen, peroxide salts such as calcium, magnesium, sodium peroxides, perborate, and percarbonate may be used as the reactant with a metal catalyst selected from transitional metals. Alternatively, a peroxygen donor, a transition metal, and an acid may be used as the reactants. The peroxygen donor may be, for example, a metal peroxide salt. The transition metal may be chelated. The acid may be an inorganic acid salt or an un-reducible organic acid selected from succinic acid or malonic acid.

8) Peracid

Where the target product is a peracid, the reactants may include an alkaline peroxide donor and a peracid precursor. The peracid precursor contains at least one acyl donor, e.g. an organic peroxide. Alternatively, the reactants may include a carboxylic acid anhydride, a peroxygen donor, and an acid donor.

9) N-halo-sulfamate

Where the target product is N-sulfamate, the reactants may include a peroxygen donor, a halogen donor, and N-sulfamate. The peroxygen donor may be potassium monopersulfate.

Optional Components in the Reactor

1) Fillers

Fillers can be used or altogether omitted depending on the type of processing and the requirements of the use of the final product. Fillers are typically inorganic compounds such as various mineral salts, metal oxides, zeolites, clays, aluminates, aluminum sulfate, polyaluminum chloride, polyacrylamide, and the like. Chlorides, carbonates, bicarbonates, oxides, and sulfates of sodium, potassium, lithium, calcium, and magnesium in various combinations may also be used as fillers.

2) pH Buffers

A pH buffer, which is an optional component of the reactor 10, provides a source of pH control within the reactor. Even when alkaline water from laundry wash is used to dissolve the reactants, the pH buffers provide effective adjustment and control of the pH within the desired range to induce the desired reactions inside the reactor. PH buffers can be inorganic (e.g. sodium bisulfate, sodium pyrosulfate, mono-, di-, tri- sodium phosphate, polyphosphates, sodium bicarbonate, sodium carbonate, boric acid, sulfamic acid and the like). Organic buffers are generally organic acids with 1-10 carbons such as succinic acid.

When used with a gel-forming material, the pH buffer may be combined with the gel-forming material or supplied by the main solvent. Alternatively, the pH buffer may be mixed with the reactant(s). The pH buffer may be an alkali, such as a mineral alkali salt, borax, silicate, or aluminate. The alkali may also be combined with boric acid. Alternativley, the pH buffer may be an organic or inorganic acid.

3) Stabilizers

Stabilizers are added when N-hydrogen donors are applied to generate N-halo-imides in-situ. Examples of stabilizers include but are not limited to N-succinimide, N-sulfamate, isocyanuric acid, hydantoin, and the like. When stabilization is not required to generate these compounds, they can be omitted.

4) Cross-linking Agents

Cross-linking agents, which are additives that change the physical or chemical properties of the composition, may be added to the reactor to control (e.g., reduce) the dissolution rate of the composition. For example, glycoluril is effective at bonding with hydroxyl and carboxylic acid groups such as those found in the cellulose of hydrolysed silicates. Glycerin alters the water permeation rate of polyvinyl alcohol. Therefore, these types of agents can be added or left out depending on the final dissolution rate, hygroscopicity, chemical resistance to oxidizers, etc.

A cross-linking agent is mixed with the binder, and the mixture is combined with the reactants in the manner described above. In cases where curing is required to set the cross-linking agent, the binder and the cross-linking agent are combined in the presence of a solvent and/or a curing agent, mixed, and reacted. If needed, the mixture is dried prior to application (e.g., being combined with the reactants).

5) Stiffening Agent

The stiffening agent, which is used to add rigidity to the gel structure, does not have to be but is preferably soluble in the main solvent. Where the main solvent is water, for example, the stiffening agent may be a water-soluble silicate such as sodium metasilicate. Other materials that may be used as the stiffening agent include borax, cationic electrolyte. Where the stiffening agent is not soluble in water, it may be hydrocarbon-based wax, a mineral salt of hydrocarbon-based carboxylic acid having at least a carbon structure and at least one a 16-carbon carboxylic acid functional group. Insoluble silicate may also be used.

6) Effervescing Agent

The effervescing agent may release carbon dioxide or contain bicarbonate.

A. Binder Structure

FIG. 1 is an exemplary embodiment of reactor 10 in accordance with an embodiment of the invention. Although the reactor 10 in this exemplary embodiment is cylindrically shaped, the invention is not so limited. The reactor 10 is an agglomerate composition containing one or more reactants 12 and a binder material 14. Although the reactants 12 and the binder material 14 are shown only for a solvent interface 16 of the reactor 10, they are preferably present throughout the reactor 10. The binder material 14 forms a colloidal gel when it comes in contact with the main solvent. Thus, when the reactor 10 is placed in contact with the main solvent, the binder material in the parts of the reactor 10 that come in contact with the main solvent will form walls of colloidal gel that divide the wet parts of the reactor 10 into multiple reactor chambers. The colloidal gel allows some permeation of the main solvent and other fluids across it, but in a restricted manner. Although only one interface 16 is shown in this example for simplicity of illustration, there may be multiple interfaces between the reactor 10 and the main solvent; in fact, the reactor 10 may be placed in a bulk body of main solvent.

Figure 2:
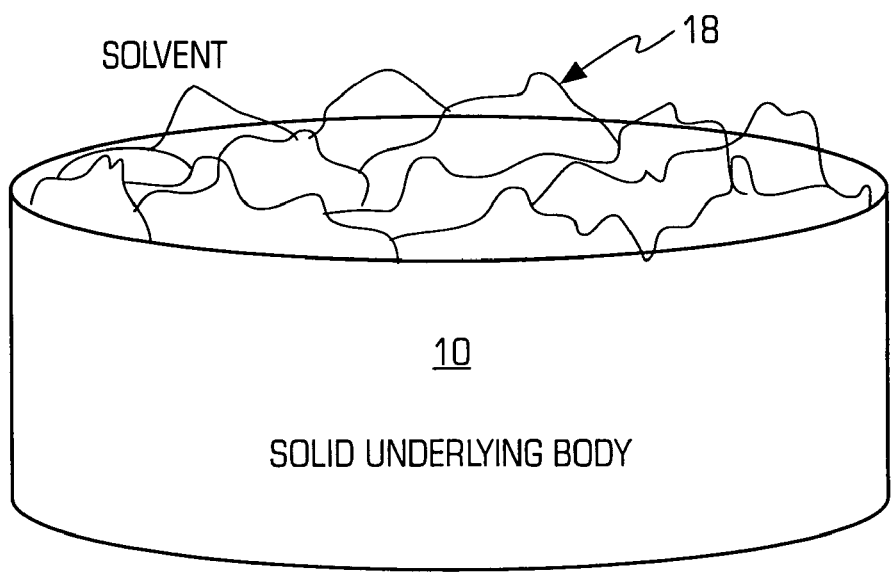
FIG. 2 is the reactor of FIG. 1 after the solvent interface has been exposed to the main solvent.

FIG. 2 is the reactor 10 after the solvent interface 16 has been exposed to the main solvent. As shown, colloidal gel 18 is formed at the interface between the main solvent and the reactor 10. The colloidal gel 18, which forms reaction chambers at the interface 16, restricts the diffusion of fluids across it. Thus, the environment inside of the reaction chambers is different from the bulk main solvent body outside the reactor 10. The environment inside the reactor 10 is more conducive to efficient target product generation than the bulk main solvent environment. While the colloidal gel walls form in parts of the reactor 10 that is in contact with the main solvent, the dry parts of the reactor 10 retain their original form.

Figure 3:
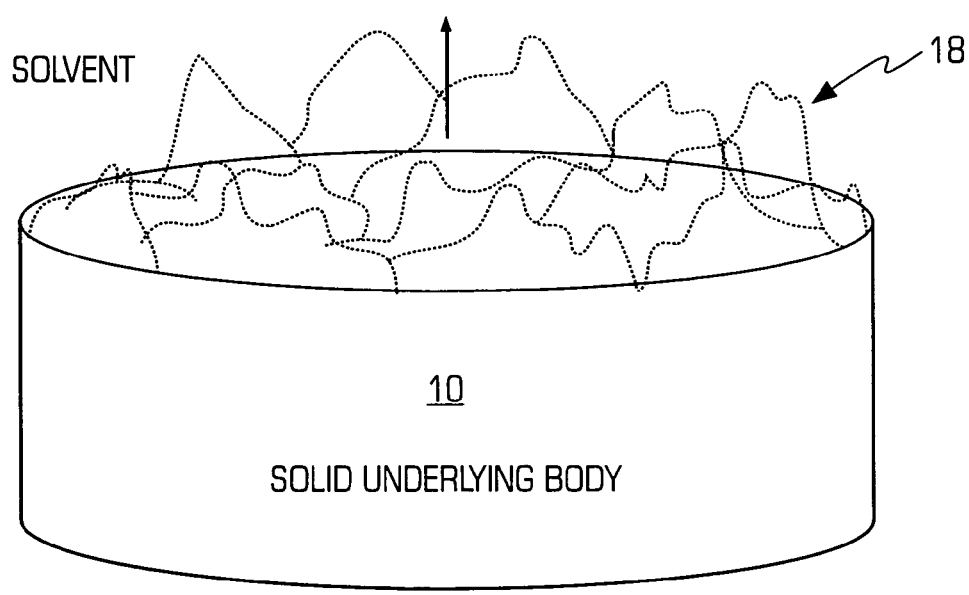
FIG. 3 is the reactor of FIG. 1 after the reactant concentrations inside the activated reaction chambers have reached the depletion level.

FIG. 3 is the reactor 10 after the reactant concentrations inside the activated reaction chambers have reached the depletion level. When the depletion level is reached, the colloidal gel walls 18 that form the reaction chambers begin to disintegrate, as shown with dotted lines to indicate the disappearance of the colloidal gel. The target product that was produced in the reaction chambers are released when the colloidal gel walls 18 disintegrate.

Since the colloidal gel walls prevent the main solvent from contacting the deeper portions of the reactor 10, the reactants 12 and the binder 14 underneath the interface 16 remain substantially dry while the first layer of colloidal gel reaction chambers are generating the target product. The disintegration of the colloidal gel walls 18, however, causes the layer of reactants and binder mixture that was under the colloidal gel layer to come in contact with the main solvent. This newly exposed part of the reactor 10 then contacts the main solvent, forms another set of colloidal gel walls, generates the target product, and releases the target product. The next level of reactants-and-binder mixture then comes in contact with the main solvent, and the generation and release of the target product continues as layers of the reactor 10 are "dissolved away" into the main solvent body.

The invention includes a method of preparing the reactor. The reactor produces high concentrations of one or more target products that are different from the reactants that are initially present in the reactor. The method of the invention allows the production of compositions that are stable for storage and, upon activation by contact with the solvent, produce a target product in a high yield. There are a few different methods for making the reactor 10 of the invention, and some of the different methods produce different embodiments.

One of the methods for preparing the reactor 10 entails mixing the reactants with binders and/or fillers and feeding the mixture to an agglomerating equipment. Once fed to the agglomerating equipment, a pressure of about 1,000 to about 10,000 psig is applied. The pressure makes the binder-reactant mixture agglomerate. The exact pressure to be applied is determined based on the final composition, the desired density of the resulting agglomerate, the desired dissolution rates, and the like. If desired, the agglomerate may be ground or crushed to achieve the desired particle size. The type and the amount of binders and/or fillers that is used depends on the desired size of the reactor and the oxidizing power. For example, a reactor having a lot of filler will have a weaker oxidizing power than a reactor of comparable size that is constituted mostly of reactants.

In an alternative method, the reactants are first mixed to form an agglomerate. There are various different ways to form the agglomerate. For example, a spray tower that is commonly used to agglomerate detergents, etc. may be used. This agglomerate can then be mixed with binders and/or fillers to be agglomerated (for the second time) into a tablet, etc. This way, the reactants are already agglomerated and the binder surrounds the reactants to form reaction chambers. In another example where the reactants, and binder, and/or the filler are all combined at once, the reactants may be separated and need to migrate before a reaction can take place.

The agglomerate of reactants (with or without binders) is granulated or crushed to form small pieces, or granules, containing the reactant mixture. If the agglomerate already has a binder layer surrounding them, the binder layer may be broken during the granulation/crushing process. However, the granules are again combined with the binder material to form a reactant-binder mixture, and a pressure between about 1,000 to about 10,000 psig is applied to the mixture to form the agglomerate composition.

Examples of equipment suitable for producing the agglomerate composition in the above methods include a compactor, an agglomerator, a roll compaction, a briquetting/tableting tool, an extruder, and the like. These suitable equipment is obtainable from Hosokawa Micron Corporation.

Figure 4:
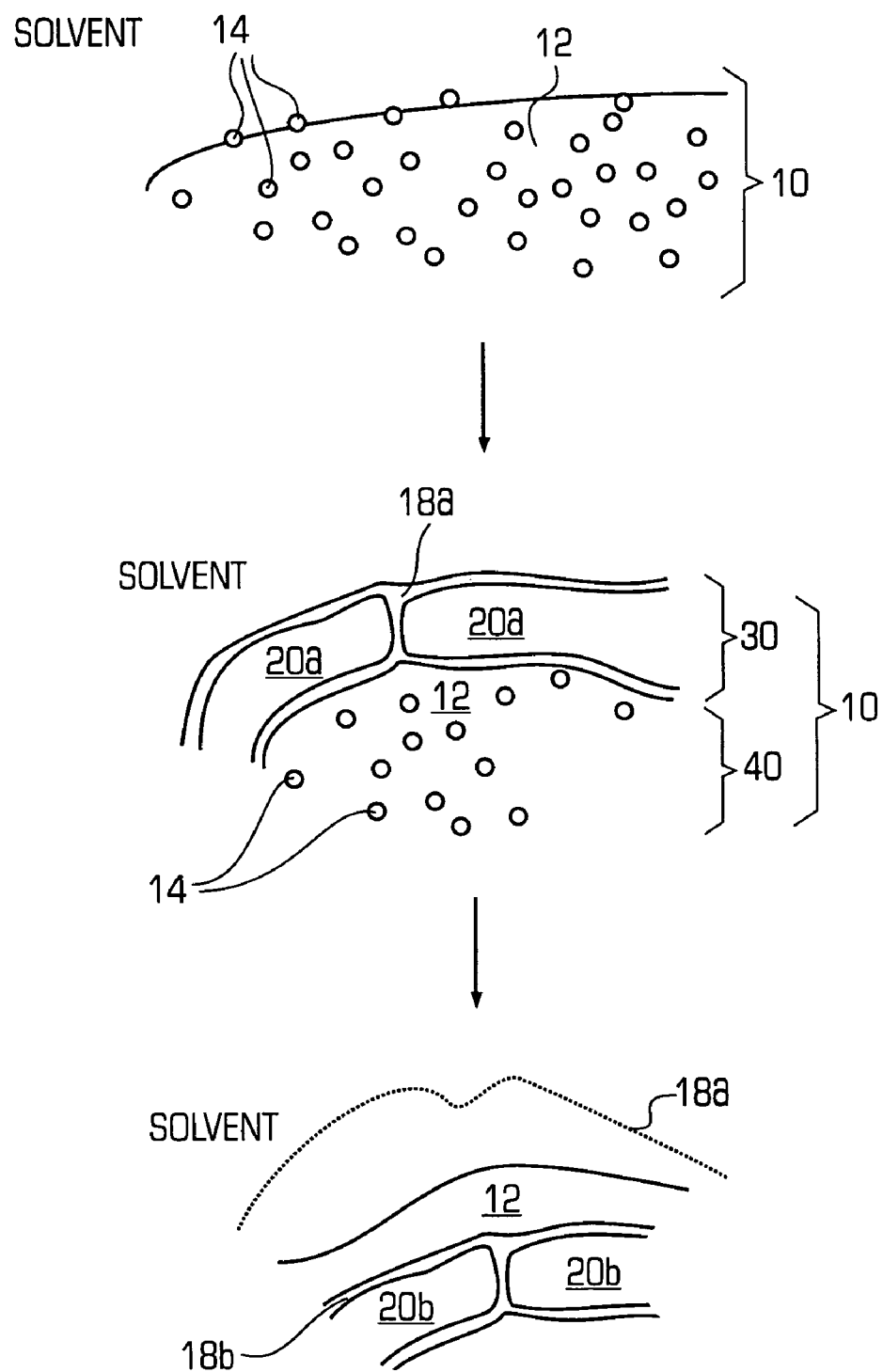
FIG. 4 shows the changes at the solvent interface for a first embodiment of the reactor made with a binder.

FIG. 4 shows the changes at the solvent interface 16 for a first embodiment. This first embodiment may be prepared by mixing the binder and the reactants before forming an agglomeration. As shown, a reactor 10 containing the reactants 12 and the binder material 14 in an agglomerated form are initially placed in contact with the main solvent. As the binder material 14 absorbs the solvent and swells up, first colloidal gel walls 18a form, creating first reaction chambers 20a. The reactants 12 usually include an oxidizer reactant, an oxidizable reactant, or both. The first colloidal gel walls 18a allows fluid permeation but in a restricted manner. Thus, while the reactants 12 dissolve in the permeated solvent and chemical reactions are generating the target product in the first chambers 20a, a section 40 of the reactor 10 retains its dry form. The target product that is generated in the first reaction chambers 20a leave the reaction chambers 20a at a controlled rate. Once the depletion level is reached, the colloidal gel walls 18a disintegrate and disappear, as shown by the dotted lines in FIG. 4. The disintegration of the colloidal gel walls 18a exposes a new part of the reactor 10 to the main solvent. If some of the reactants 12 are directly exposed to the solvent, they will dissolve and react to generate the target product, but this chemical reaction will not have a yield as high as if it had occurred under the sheltered environment of the colloidal gel reaction chambers. The binder material 14 absorbs the main solvent and forms a colloidal gel wall 18b, forming another set of reaction chambers 20b. Once the colloidal gel walls 18b are formed, the main solvent permeates into the reaction chamber 20b in a controlled manner. The reactants 12 in the chamber, activated by this main solvent, generate the target product and the target product is released at a controlled rate. When the depletion level is reached, the colloidal gel wall 18b disintegrates (not shown) and releases the generated target product into the bulk solvent body. Since only a portion of the reactor 10 generates the target product at a given time, a gradual time-release of the target product is achieved.

Figure 5:
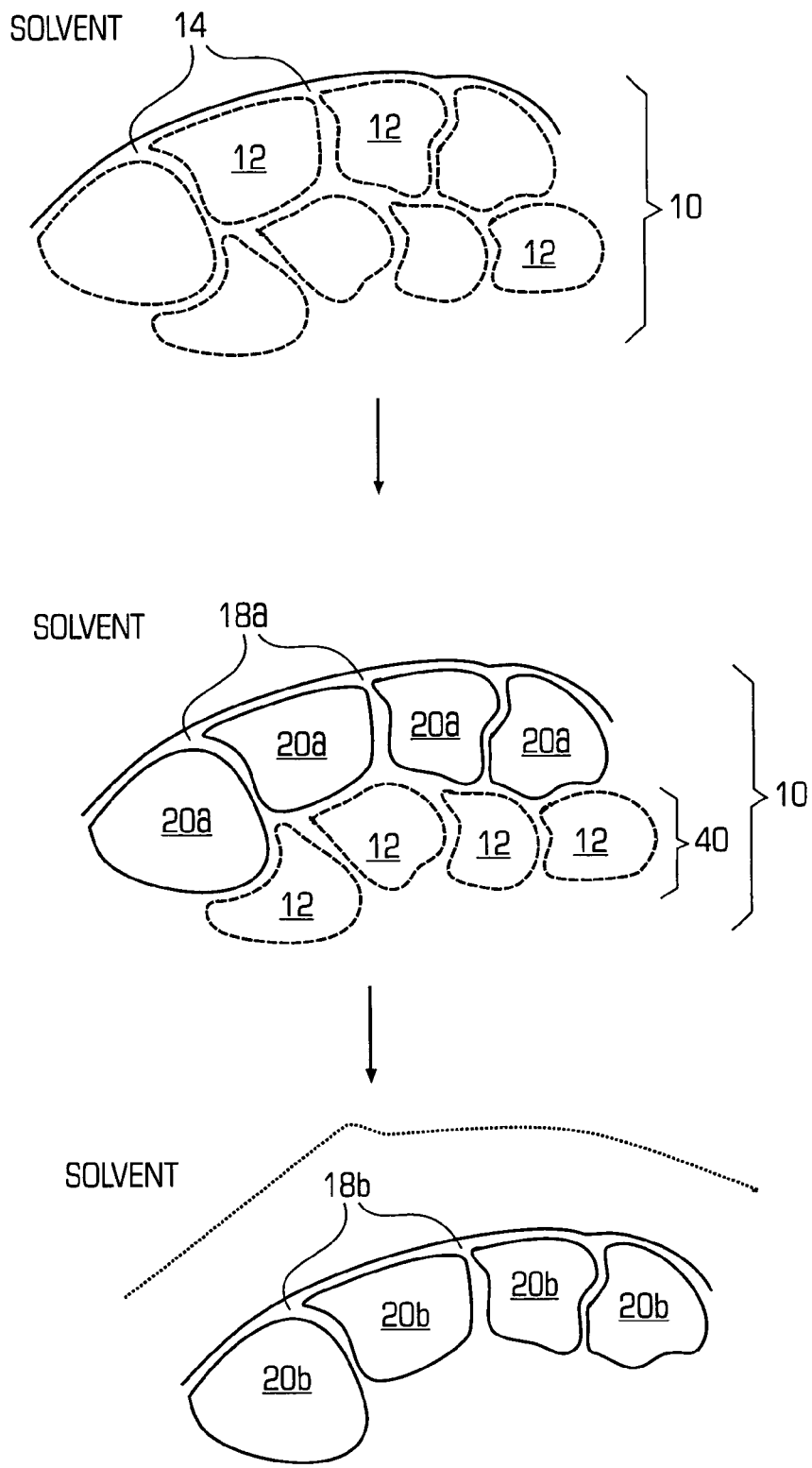
FIG. 5 shows the changes at the solvent interface for a second embodiment of the reactor made with a binder.

FIG. 5 shows the changes at the solvent interface 16 for a second embodiment. This second embodiment may be prepared by forming granules of reactants, coating and/or mixing the granules with binders, and applying pressure to agglomerate the binder-coated granules. As shown in FIG. 5, the outlines of the pre-agglomeration granules can be seen, defined by the binder material 14. When the reactor 10 is placed in contact with the solvent, colloidal gel walls 18a form near the outer areas of the reactor 10 where the binder material absorbs the solvent. The formation of the colloidal gel walls 18a creates first chambers 20a while the section 40 of the reactor 10 maintains its original form. The solvent continues to permeate through the colloidal gel walls 18a, dissolving the reactants 12 in the chambers 20a and triggering a chemical reaction that generates the target product. The target product permeates out of the chambers 20a, preferably in a solution form. Eventually, the first chambers 20a reach the depletion level and disintegrate, as shown by the broken line indicating the original outline of the reactor 10. When the first chambers 20a disintegrate, the solvent comes in contact with the next layer of reactants and binder material, and forms a second colloidal gel wall 18b. The second colloidal gel wall 18b forms a set of second chambers 20b, which then generate the target product.

One way to control the timing of the colloidal gel disintegration is to use a binder material so that the colloidal gel has a lower solubility than the reactants in the chamber.

Although the figures only show the reactants 12 and the binder material 14, there may be additional layers deposited on the reactor as indicated herein. For example, a protective coating layer such as one that contains a polymer, polysaccharide, polysioxane, polyvinyl alcohol, or silicate may be deposited on the outer surface of the reactor 10 to shield the reactor 10 from moisture, etc. during storage. Other components such as pH buffer and filler may also be used as desired, and they are described in detail below.

Generally, the reactants are broken down as about 1-90 wt. % oxidizer reactant and about 1-50 wt. % oxidizable reactant. The remainder of the body contains 20-90 wt. % binder and 0-40 wt. % pH buffer, with the remainder being fillers to achieve a total value of 100 wt. %.

Binder Material

Binders are combined with the reactants to form a mixture. Binders, upon exposure to the main solvent, form a colloidal gel that is permeable to the main solvent. Examples of binder material include water-soluble silicates, aluminum sulfate, aluminates, polyaluminum chloride, polysaccharides including cellulose, chitosan and chitin, and absorbent polyacrylic polymers and copolymers such as Carbopol®. A poloxamer block copolymer such as Poloxamer 407 sold by BASF under the trade name Lutrol® F127, polyvinyl alcohol with or without borax, or polyacrylamides may also be used.

Silicates make effective binders for holding the reactants in place and restricting the release of reactants until the desired oxidant is produced. Silicate-based coating material may be something that contains silicate, such as metasilicate, borosilicate, and alkyl silicate. Under low-pH conditions, the silicates remain colloidal; however, when the acid-catalyzed conditions induced by the reactants is depleted, the colloid dissipates. Upon dissipating, various polysaccharides such as cellulose and chitosan form permeable gel barriers that can effectively function as reactor walls. Certain polymers such as water absorbent polyacrylates and their copolymers can also form gels. One example is Carbopol® sold by Noveon, Inc. located in Cleveland, Ohio.

How suitable a particular binder material is for a given application depends on the surrounding conditions. For example, silicate coatings are well established for providing a barrier film of protection to percarbonates and other bleaching agents used in laundry detergents but do not always make a reactor. In laundry detergents, the inclusion of bleach precursors such as tetraacetyl-ethylenediamine or nonanoyl-oxybenzene sulfonate to enhance the bleaching performance in low temperatures is common. The hydrolysis of the precursors requires alkaline pH conditions. In such applications, due to the hydrolysis requirements and peroxygen chemistry, the internal and external solution used to dissolve the reactants is high in pH. The silicate coating is soluble under alkaline conditions, and the integrity of the reactor wall is compromised. The coating dissociates rapidly, without acting as a reactor. In this case, the benefit of the high reaction yield is not achieved.

Silicates provide for a simple and inexpensive reactor coating when used in lower pH applications or formulations that result in internal acidic pH conditions that sustain the integrity of the reactor wall. This usefulness of silicates remains uncompromised even if the external conditions are alkaline in pH, such as in the case of laundry water. Silica solubility is poor at low pH. At lower pH, silica remains colloidal and forms a colloidal gel. When monopersulfate (MPS) and a source of chloride such as NaCl are encased within a coating of silicate such as sodium silicate, then added to water, the water permeates through fissures and cracks in the coating and dissolves the reactants. The resulting low pH (<5) from the dissolving MPS suppresses the dissolution rate of the surrounding silica, and the silica remains as a colloidal gel.

Inside the space enclosed by the silica gel barrier, the concentration of reactants remains high and the resulting reactions produce high yields of chlorine gas. Upon diffusion of the reactants and the chlorine into the surrounding water, hypochlorous acid and hypochlorite ions form as a function of the water's pH. The resulting conversion to the target product is therefore much higher when the pH inside the reactor is low and the reactor wall remains undissolved. With the inclusion of N-succinimide, it is now possible to produce N-chlorosuccinimide with the slow-diffusing chlorine gas. pH buffers can be added to further ensure efficacy based on application requirements. In alkaline pH conditions such as laundry bleaching, the elevated pH will not allow for generation of target products like N-chlorosuccinimide. By sustaining the integrity of the reactor, the internal conditions of the reactor are such that the reactions are successfully carried out. The target product is efficiently generated and released.

B. Gelatinous Structure

The binder structure described above works sufficiently well for slowing down the dissolution rate of the tablet and improving the sustained release of the agents from the tablet. However, in the case of in-situ generated oxidants where the tablet is immersed in excess diluting solvent, an agglomerate that is held together by binders may break apart as the reactants dissociate, compromising the binder's hold on the remaining reactants.

Viscosity modifiers may be used as an alternate "binder" for the agglomerate. Viscosity modifiers are well known materials used for a variety of applications including thickening solutions for forming suspensions (e.g., dishwashing detergents, oral medications). Gels are often produced using viscosity modifiers but differ from suspensions in physical properties and structures. While a viscosity modifier can increase the viscosity of a solution such as in the case of a suspension, the suspension readily disperses upon exposure to excess dilution and in particular upon mixing with excess diluting solvent. A gel, however, can be made to withstand rapid dispersing under identical conditions and maintain its gel-structure even when exposed to various levels of mixing.

A tablet may be prepared with a gel-forming material that forms a gelatinous structure when exposed to the main solvent. When the gelatinous structure is formed, so do chambers, as described above. The chambers contain reactants that produce the target product from an in-situ chemical reaction, allowing for substantially higher yields of product than tablets having equivalent mass with no gel-forming additive. The gelatinous structure may disintegrate and dissipate after the chamber contents are depleted.

Figure 6:
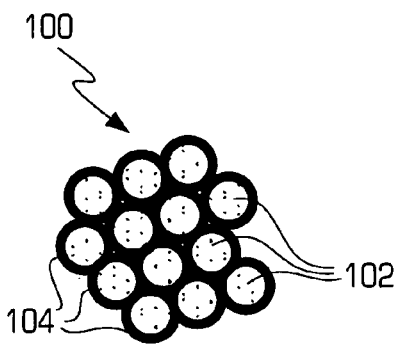
FIG. 6 is a diagram of one embodiment of the gelatinous structure in accordance with the invention.
Figure 7:
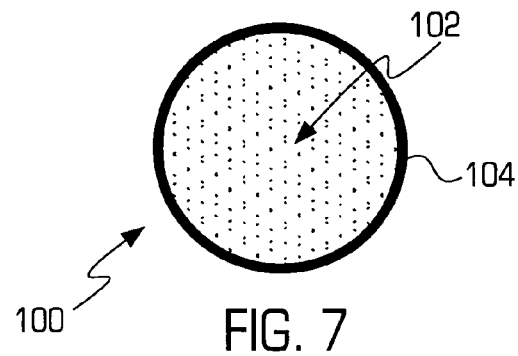
FIG. 7 shows a close-up of one of the granules in FIG. 6.

FIG. 6 is a diagram of one embodiment of a gelatinous structure 100 in accordance with the invention. This embodiment, shown as agglomerated granules, includes an agglomeration of granules 102, each of which is coated with a gelling agent 104. FIG. 7 shows a close-up of one of the granules 102. Each of the granules 102 contains one or more reactants that, upon exposure to a main solvent, generates a desired target product. The gelling agent 104 contains a gelling agent that is solid when dry but forms a gel layer upon contacting the main solvent.

There are many types of gel-forming materials that are suitable for incorporation into the gelling agent 104. Some of the common ones are Carbopols® (now known as carbomers), carboxymethylcellulose. ethylcellulose, hydroxyethylcellulose, hydroxypropyl cellulose, Veegum®, methylcellulose, poloxamers (Pluronics®), polyvinyl alcohol, sodium alginate, tragacanth, and xanthan gum. Though each gel-forming material has some unique properties, there are some generalizations that can be made. The gel-forming materials may be categorized into four groups: natural hydrocolloids (also referred to as "gum"), semisynthetic hydrocolloids (also referred to as "polysaccharides"), synthetic hydrocolloids, and clay. Some examples of natural hydrocolloids include acacia, tragacanth, alginic acid, carrageenan, locust bean gum, guar gum, and gelatin. Examples of semisynthetic hydrocolloids include methylcellulose and sodium carboxymethylcellulose. Examples of synthetic hydrocolloids (also referred to as "polymers" including polymers, crosslinked polymers, and copolymers) include Carbopol®, and examples of clay (including swelling clay) include bentonite and Veegum®.

Figure 8:
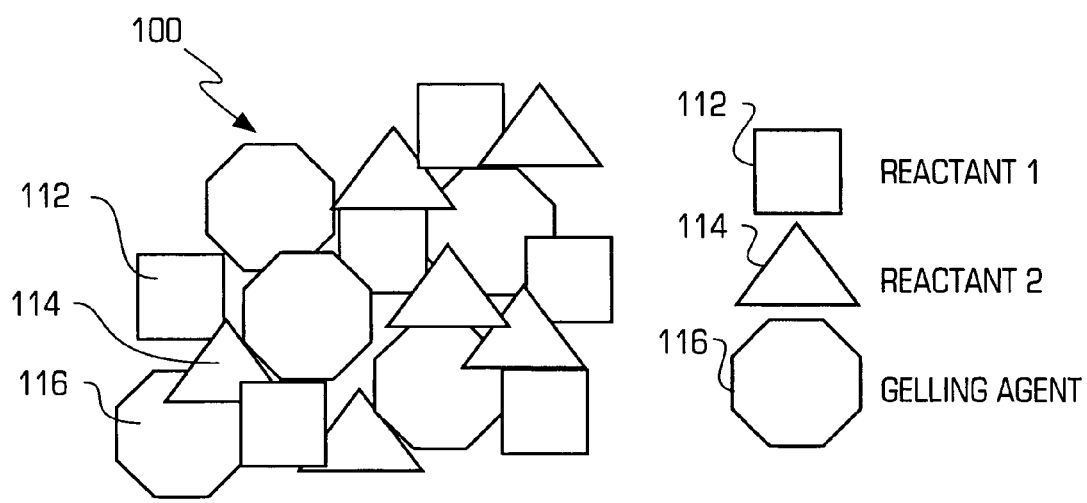
FIG. 8 is a diagram of another embodiment of the gelatinous structure in accordance with the invention.

FIG. 8 is a diagram of another embodiment of the gelatinous structure 100 in accordance with the invention. The gelatinous structure 100 of this embodiment is also referred to as a "tablet," since it may be made available in the form of tablets. As shown, this embodiment is an agglomeration of reactants—a first reactant 112, a second reactant 114, and a gelling agent 116 are agglomerated into a cluster. Unlike the embodiment of FIG. 6, where the gelling agent is coated on a cluster of reactants in the form of the gelling agent 104, the gelling agent is intermixed with the reactants in this embodiment. Any gelling agent that is suitable for the first embodiment may be used for the second embodiment.

Figure 9:
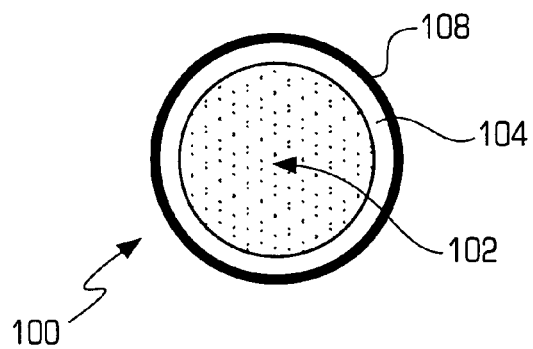
FIG. 9 is a diagram illustrating that the granules of the embodiment shown in FIG. 6 may be coated with an environmentally protective coating in addition to the gelling agent.

FIG. 9 is a diagram illustrating that the granules 102 of the embodiment shown in FIG. 6 may be coated with an environmentally protective coating 108 in addition to the gelling agent 104. The environmentally protective coating 108 may be polyvinyl alcohol (PVA), a water-soluble silicate (e.g., sodium metasilicate, borosilicate), a polymer, or a polysaccharide. Preferably, the coating 108 is soluble in the main solvent so that when the gelatinous structure 100 is placed in contact with the main solvent, the coating 108 dissolves and exposes the gelling agent 104 to the main solvent. The gelling agent 104 allows restricted permeation of the main solvent to the reactant-containing granules. When the reactant(s) dissolve in the main solvent, a chemical reaction takes place that results in the generation of the desired target product.

Figure 10:
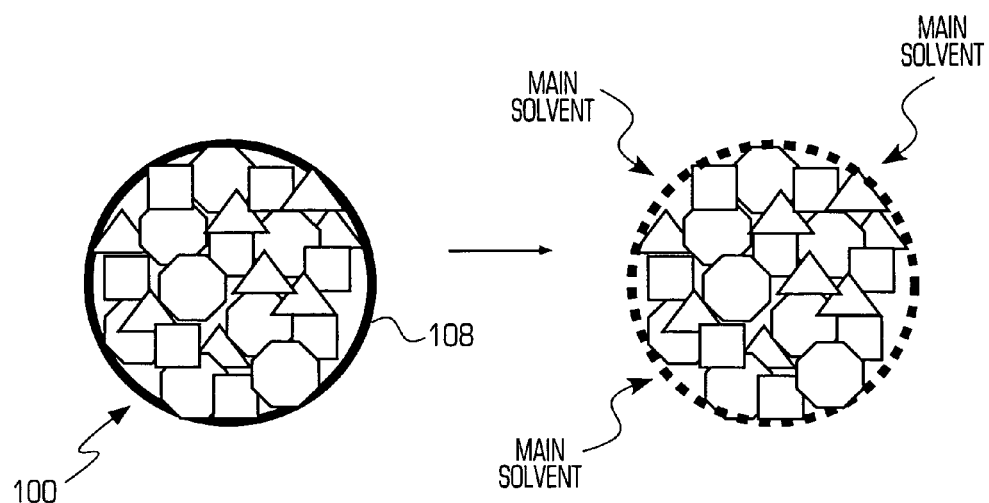
FIG. 10 is a diagram illustrating the composition of FIG. 8 coated with the environmentally protective coating.

FIG. 10 is a diagram illustrating the gelatinous structure 100 of the embodiment in FIG. 8 coated with the environmentally protective coating 108. As shown, the coating 108 dissolves when the agglomerated reactants 110 is exposed to the main solvent. The main solvent then reaches the reactants and triggers the chemical reaction that generates the target product.

Figure 11:
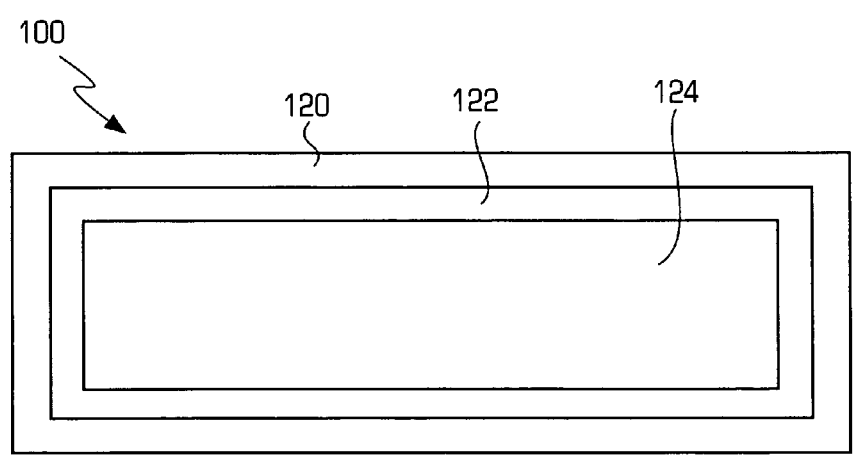
FIG. 11 is a conceptual diagram illustrating the viscosity profile of the composition when placed in the main solvent.

FIG. 11 is a conceptual diagram illustrating the viscosity profile of the gelatinous structure 100 when placed in the main solvent. As shown, there are three general regions that are characterized by viscosity ranges. An outermost region 120, which is in direct contact with the surrounding main solvent, is a gel structure with reduced viscosity. The intermediary region 122, which is exposed to some of the main solvent that permeated through the outermost region 120 in a restricted manner, is a gel structure with a high viscosity. An inner region 124 is a yet-undispersed and substantially dry gel-forming composition in the form of granules 102 or agglomerate. Although the diagram makes it seem like there are clear boundaries dividing the three regions for simplicity of illustration, the three regions are in the form of a viscosity gradient.

Using the gelatinous structure 100 of the invention, water-soluble compositions for generating chlorine dioxide can be produced that yield concentrations of chlorine dioxide over 250% more than the existing water-soluble compositions. Further still, the disclosed invention increases the weight % yield of chlorine dioxide by over 30% above the existing compositions that are made of or produce water-insoluble constituents. Water-soluble gels provide superior improvement over the existing compositions that utilize high concentrations of inert materials (e.g., swelling clays) to construct a porous structure.

Gel forming additive technology can be readily assimilated into other in-situ generating tablets to achieve the same benefits in yield by increasing the weight % of reactants in the agglomerate composition, and resulting in an increase in the weight % yield of desired product.

The invention is based on the use of substantially low levels of gel-forming material that bind and hold the reactants together while immersed in the main solvent, thereby maintaining the structural integrity of the agglomerate composition. The gel, which is formed when the gel-forming material contacts the main solvent, restricts the diffusion of the reactants until the reaction is near complete. After the reaction is substantially complete, the gel disintegrates. The gel-forming material may be a polymer or copolymer that increases solution viscosity, and at least one component that enhances gel formation and rigidity.

The gel-forming materials are particularly useful in producing self-sustaining tablets that produce high yields of in-situ generated oxidants. The use of this gel-forming technology dramatically reduces the quantity of inert materials used to improve reaction kinetics in prior art, and substantially increases the "weight % yield" of the tablet when compared to tablets incorporating currently known methods.

Without limiting the invention, useful components used in forming water-soluble gels include: water-soluble silicate such as sodium metasilicate, polymers such as PVA or cross-linked polyacrylates sold under the trade name Carbopol® by Novean, and copolymers such as polyoxyethylene polyoxypropylene block copolymer sold under the trade name Lutrol® by BASF, polysaccharides, pH buffers such as alkali or acids, and coagulating agents such as sodium aluminate.

Composite gels are particularly useful in that small quantities relative to the total mass of the agglomerate composition dramatically improve the structural integrity of the agglomerate when immersed in water, and improve the weight % yield of the agglomerate composition. Composite gels contain at least two additives that, when combined, produce a gelatinous structure having a viscosity substantially higher than that obtained using either additive alone when exposed to the same pH conditions. Composite gels are produced by combining a viscosity-increasing material with an additive that enhances the formation and rigidity of the gel. For example, a composite gel may be a combination of a polymer and a silicate, a combination of two or more gel-forming materials, or a combination of PVA and borax. When composite gelling agents are used, the number and types of compounds that can be used increases. Also, the amount of viscosity modifying agent can often be substantially decreased.

For example, while PVA increases the viscosity of the solution, it does not form an effective gel alone. Elvanol® sold by DuPont typically shows a viscosity profile of up to approximately 2,000 centipoise at a 10 wt. % solution. However, combining borax or boric acid with an alkali and the PVA produces a gelatinous composite having a viscosity over 100,000 centipoise. Composites can also be produced by combining multiple gel-forming materials to produce a gel of substantially higher viscosity than when the compounds are used with pH buffers as illustrated in the examples.

A hydrocarbon having a low solubility in the main solvent may be incorporated into the gelatinous structure 100. The hydrocarbon may be ethylene wax, oxidized ethylene wax, polyolefin wax, paraffin wax, microcrystalline wax, mineral salts of stearate, mineral salts of palmitate, or mineral salts of hydrocarbons having at least 16 carbons and at least one carboxylic acid group. The low-solubility hydrocarbon may function as a binder in the gelatinous structure 100, holding the components together when the gelatinous structure 100 is immersed in the main solvent. The low-solubility hydrocarbon may also act as a stiffening agent that increases the rigidity of the gelatinous structure.

Gelatinous Structure

In the gelatinous structure capable of producing in-situ generated oxidants in high yield, the viscosity of the gel is sufficiently high to prevent diffusion of the reactants and gel even under conditions that would normally induce rapid dilution. The viscosity being sufficiently high also helps maintain the structural integrity of the agglomerate as to prevent a premature breakup of the agglomerate composition when immersed in excess diluting solvent. The gel rigidity is preferably at a level that is sufficient to prevent rapid dispersion of the agglomerate even when agitation or circulation of the water occurs. To achieve this, it is desirable to utilize a gel-forming chemistry that produces a "gelatinous structure" within the agglomerate. This gelatinous structure has a viscosity greater than about 5,000 centipose, preferably greater than about 50,000 centipoise, and preferably greater than about 100,000 centipoise. It is desirable that the rheology within the high viscosity gel-structure have pseudoplastic characteristics, such that upon shaking or jarring, the agglomerate does not break up as would be expected if the gel-structure possessed the behavior of a thixotropic material. As the outer layers of agglomerate react and dissipate, the gelatinous structure will experience increased dispersion, the viscosity will decrease with time and dilution, and the gel-structure may take on thixotropic characteristics.

The gelling agent constitutes no more than 10 wt. % of the gelatinous structure 100, preferably constitutes less than 1 wt. % of the gelatinous structure 100, and preferably constitutes less than 0.5 wt. % of the gelatinous structure 100.

The gelatinous structure 100 may be two-phase or single phase. The "single-phase" gel structures maintain the structural integrity of the agglomerate better than the single-phase gels. While "two-phase" gels can be used, practical limitations would require substantially more gel-forming material to prevent dispersion of the agglomerate, and/or will limit the utility of the agglomerate to applications having low-flow conditions, or lower levels of diluting solvent.

EXAMPLE 1

0.6 grams of sodium metasilicate is dissolved in 100 mL water. Acid is added to reduce the pH to 6.5, at which point a colloidal silicate forms. The viscosity of the solution remains sufficiently low such that the solution is readily pourable.

EXAMPLE 2

0.6 grams Carbopol® is combined with 100 mL of water and dispersed, followed by pH increase with NaOH to achieve the gel point. The viscosity is high but the gel remains pourable.

EXAMPLE 3

0.4 grams Carbopol® was combined with 0.2 grams of ground sodium metasilicate. The mixture was sprinkled into 100 mL of vigorously mixed water while measuring pH. Once added, the pH increased to approximately 10.5, then quickly but steadily dropped until a final pH of 6.5 was achieved. After approximately four minutes, the viscosity exceeded the magnetic stirrer capacity to agitate the gel. After six minutes, the clear gel produced was un-pourable and remained in the beaker while the beaker was inverted.

The gel produced from the Carbopol®-silicate composite was substantially higher in viscosity and substantially more rigid than that produced by either equivalent weights of silicate or Carbopol® alone.

At the pH range of approximately 4-7, the water-soluble silicate is converted to a colloidal suspension, and the Carbopol® viscosity increases. Combined, it is theorized that the colloidal silicate, when intimately dispersed in the polymer gel, further stiffens the gel as the gelatinous structure forms by producing a three-dimensional structure of interlacing particles or solvated macromolecules that restrict the movement of the dispersing medium.

Other additives such as sodium aluminate or higher concentrations of alkali salts can replace the water-soluble silicate in the composite. Once adequately diluted, the gel components dissipate and/or completely dissolve in the water.

When the gel-forming material is intimately mixed with the reactants making up the composition, it is expected that the reactants themselves induce the formation of a two-phase system until such time the reactants completely dissociate and react to produce the desired product. When the dissociated reactants produce the desired product, it is expected that the gel-structure will alter its rheology and take on more pseudoplastic (single-phase) properties.

Adding the Gelling Agent

The gelling agent is effectively dispersed or distributed within the agglomerate to be effective. If the gelling agent is added to the dispersing medium (water) in a haphazard manner, there is a tendency for the agent to "clump." The outer molecules of the gelling agent contact the medium first and hydrate, forming a surface layer that is more difficult for the medium to penetrate. The clumps will ultimately hydrate but it will take more time. It is therefore preferable to distribute the gelling agent with the reactants prior to producing the final agglomerate (tablet). The gelling agent can be applied to the mixture of reactants prior to agglomeration, or in the case of granulation, after granulation prior to agglomeration. In an alternative method, the gelling agent can be applied to both the powdered mixture and the granules.

It is also beneficial to have additional additives that enhance the formation of the gel and/or increase the rigidity of the gel in intimate contact with the gel-forming material when the solvent begins hydrolyzing the gel-forming material. To do this, the additives, such as those used in forming composite gels, are effectively combined with the gel-forming agent, and are considered to be included with the gelling agent as described above. In the case of pH modifiers that induce gel formation as in the case of synthetic polymers such as Carbopol® the pH modifier can be combined with the Carbopol®, provided by the reactant composition, or be naturally provided with the water, such as natural acquiring alkalinity.

This technology has great utility in slowing the release of traditional oxidizers such as: calcium hypochlorite, trichloroisocyanuric acid, dichloroisocyanuric acid, lithium hypochlorite, dibromodimethylhydantoin, bromochlorodimethylhydantoin, percarbonate, perborate, monopersulfate, persulfate and the like where large volumes of dilution water are present, and slow release is desired such as in cooling towers, swimming pools, toilets and the like.

None of the prior art discloses a self-sustaining tablet comprised of reactants for in-situ generation of an oxidant combined with a gel-forming material that forms a gelatinous structure and increases the yield of the oxidizer product. The advantages over the prior art are: higher concentrations of reactants in the composition, increased "weight % yield" of oxidants, elimination of reaction containers such as those disclosed in one of the Wei patents, and extended release times of in-situ generated oxidants compared to agglomerate compositions not including the gelling agent.

The reactor has far-reaching applications. Reactants such as PMPS and NaCl are quite stable when dry but once moisture is added and reactions are triggered, an agent with a completely different set of properties may be produced. The reactor allows for a stable point-of-use product with easy application. The fact that the reaction is triggered by moisture allows for a wide range of applications since the reactor remains stable until some type of liquid, such as water, contacts the composition. The contaminated liquid that is to be treated is what activates the reactor to generate and release target products for treatment. When the released target products are oxidizers, they treat the bulk liquid by controlling bacteria, viruses and various organic and inorganic contaminants.

The benefits of the invention are broad in nature. The "reactors" formed by the gelatinous structure are stable for storage and provide safe bleaching agents and antimicrobial agents in a form that is ready for use. This technology enhances the utility of the agents. For example, the agents can be combined with traditional pool water treatments to provide chlorine dioxide or hydroxyl radicals for a synergistic effect.

One benefit of the invention is to control the reactor chemistry as to maximize the concentration of reactants in an environment conducive to forming the target products. For example, N-chlorosuccinimide generation is best performed under acidic conditions where chlorine gas and/or hypochlorous acid are readily available. In applications such as laundry bleaching, generation of N-chlorosuccinimide is less than optimal because the alkaline pH (generally >9.0) is not well suited for producing N-chlorosuccinimide. By producing N-chlorosuccinimide in a contained space inside the reactor and controlling the diffusion rate of product and reactants out of the reactor, the conditions that are conducive to high conversion rates and yields are sustained. Thus, the yield is maximized prior to the product's being releasing into the alkaline bleaching environment of the wash-water. Similar characteristics are true of the various oxidizers produced by reacting reagents to generate more powerful oxidants in-situ. Conditions such as pH, concentrations of reactants, and minimizing oxidizer demand such as that found in the bulk washwater must be controlled to maximize conversion of the reactants and the yield of the target product.

The reactor 10 can be formed into any useful size and shape, including but not limited to a granule, nugget, wafer, disc, briquette, or puck. While the reactor is generally small in size (which is why it is also referred to as the micro-reactor), it is not limited to any size range.

Data

A composition comprised of 30% Dichloroisocyanuric acid, 30% sodium bisulfate, and 37.5% sodium chlorite combined with 2.5% PVA was thoroughly mixed and pressed to produce granules. The composition of these granules is referred to as "the 334 composition". The >200 but <300 split of granules was used for the following test.

Tests were conducted using varying wt. % of gel-forming material that contains 67 wt. % Carbopol® 676 and 33 wt. % ground sodium metasilicate. The gel-forming material was admixed with the granules, and the final composition was pressed into a tablet. All tablets were of the same shape, and were relatively equal in size as disclosed in the tablet.

One sample of granules was ground to produce a powder, and the powder was then pressed into a tablet with no gel-forming material.

Test Rig

A 5-gallon container was equipped with a mixer fixed in position and centered in the middle of the container, and a pH probe attached to a digital readout was immersed below the water line. A spectrophotometer calibrated for chlorine dioxide at 445 nm wavelength was set to read continually, and was zeroed before each run.

When the tablet was immersed and released into the container, the turbulence from the mixer was such that it continually swirled the tablet in approximately a 6-inch diameter circle, thereby preventing settling which can cause localized accumulation of reactants and pH that could skew the results in favor of increased chlorine dioxide yield.

A sample cell was immersed into the swirling solution at time increments noted in the table. A stop watch tracked lapsed time, and the pH was noted. The sample cell was wiped dry, placed in the photometer, and the results noted, whereby the sample was returned to the container.

Test Results

The tests show how the composition significantly influences the production of chlorine dioxide. The sample made with powder produced from the same composition as the granules used to make the other tablets produced 30% less chlorine dioxide than the tablet made from the granules.

When the gel-forming material was added to the tablets, a significant increase in Weight % Yield resulted. By adding just 1 wt. % of the gel-forming mixture to the granules prior to agglomerating into a tablet, there was a 78.5% increase in weight % yield over the tablet made from powder, and a 39% increase over the tablet made from granules without the gel-forming material.

As indicated by the tables below, the tablet produced from the 2.5% and the 5 wt. % gel-forming material retained its integrity as a tablet for an extended period of time and did not produce the peak in chlorine dioxide concentration as observed in the other samples. However, the tablet sustained the output for an extended period of time. This could prove very useful in applications where it is desirable to release the in-situ generated oxidizer over an extended period of time while immersed in water, rather than a rapid spike followed by a slow decay in concentration. Examples include cooling tower treatments, potable water treatment, toilet bowl immersed tablets, etc.

| Sample | Weight (gm) | Water volume (ltr) | mg/ltr produced | weight % Yield |
|---|---|---|---|---|
| No Gel - Powder | 2.9 | 10.5 | 28 | 10.14 |
| No Gel - granules | 2.9 | 10.5 | 36 | 13.03 |
| 0.5% Gel - Granules | 2.2 | 10.5 | 30 | 14.32 |
| 1.0% Gel - Granules | 3.0 | 10.5 | 50 | 18.10 |

|  | No Gel | 0.5% Gel |
|---|---|---|
| Start Temp (F.) | 82 | 83 |
| Start pH | 7.89 | 7.89 |
| Finish pH | 7.1 | 7.21 |
| Weight (gm) | 2.9 | 2.2 |
| Volume (liters) | 10.5 | 10.5 |
| Speed setting (1-5) | 1 | 1 |

| Lapsed Time | PPM | pH | Lapsed Time | PPM | pH |
|---|---|---|---|---|---|
| 0:00 | 0 | 7.89 | 0:00 | 0 | 7.88 |
| 0:45 | 30 | 7.10 | 0:45 | 26 | 7.18 |
| 1:30 | 36 | 7.04 | 1:30 | 30 | 7.18 |
| 2:30 | 35 | 7.07 | 2:30 | 29 | 7.21 |

|  | 1.0% Gel | 2.5% Gel |
|---|---|---|
| Start Temp (F.) | 83 | 83 |
| Start pH | 7.89 | 7.89 |
| Finish pH | 7.12 | 7.15 |
| Weight (gm) | 3.0 | 2.9 |
| Volume (liters) | 10.5 | 10.5 |
| Speed setting (1-5) | 1 | 1 |

| Lapsed Time | PPM | pH | Lapsed Time | PPM | pH |
|---|---|---|---|---|---|
| 0:00 | 0 | 7.89 | 0:00 | 0 | 7.89 |
| 0:45 | 13 | 7.57 | 0:45 | 7 | 7.7 |
| 1:30 | 38 | 7.05 | 1:30 | 14 | 7.41 |
| 2:30 | 47 | 7.04 | 2:30 | 21 | 7.27 |
| 3:30 | 50 | 7.07 | 3:30 | 25 | 7.23 |
| 4:30 | 49 | 7.12 | 4:30 | 26 | 7.21 |
|  |  |  | 5:30 | 26 | 7.21 |
|  |  |  | 7:30 | 24 | 7.22 |
|  |  |  | 9:30 | 24 | 7.15 |

|  | No Carb Powder | 5% C/S +200 |
|---|---|---|
| Start Temp (F.) | 82 | 82 |
| Start pH | 7.89 | 7.85 |
| Finish pH | 7.1 |  |
| Weight (gm) | 2.9 | 3.0 |
| Volume (liters) | 10.5 | 10.5 |
| Speed setting (1-5) | 1 | 1 |

| Lapsed Time | PPM | pH | Lapsed Time | PPM | pH |
|---|---|---|---|---|---|
| 0:00 | 0 | 7.89 | 0:45 | 2 | 7.73 |
| 0:45 | 26 | 7.06 | 1:30 | 6 | 7.65 |
| 1:30 | 28 | 7.04 | 2:30 | 10 | 7.56 |
| 2:30 | 27 | 7.07 | 3:30 | 14 | 7.51 |
| 4:30 | 15 | 7.50 |
| 5:30 | 14 | 7.48 |
| 6:30 | 14 | 7.48 |
| 7:30 | 16 | 7.49 |
| 8:30 | 16 | 7.50 |
| 9:30 | 16 | 7.52 |
| 10:30 | 18 | 7.54 |
| 11:30 | 16 | 7.55 |
| 12:30 | 16 | 7.57 |
| 13:30 | 15 | 7.58 |
| 14:30 | 14 | 7.59 |
| 15:30 | 14 | 7.62 |
| 21:30 | 12 | 7.72 |
| 22:30 | 13 | 7.74 |
| 26.30 | 12 | 7.79 |
| 28.30 | 11 | 7.82 |

In a similar test, the 334 composition disclosed above was used to produce Tablets of approximately 4.0 grams in size. A control sample was produced and contained no additives. The remaining tablets were produced to include additives at 1 wt. % to compare performance profiles of individual additives as well as combinations. One tablet was produced by first forming granules from the 334 composition, then admixing 1 wt. % of the Carbopol®/silicate ("C/S") gelling agent, then the combined mixture was pressed into a tablet. Each approximate 4.0 gram tablet was added to 14 L of water with sufficient agitation as to prevent settling of the tablet while continually monitoring the pH.

TESTING Round 2:

|  | 1% CaStearate | 1% Carb |
|---|---|---|
| Start Temp (F.) | 82 | 82 |
| Start pH | 7.85 | 7.85 |
| Weight (gm) | 4 | 3.9 |
| Volume (liters) | 14 | 14 |
| Speed setting (1-5) | 1 | 1 |

| Lapsed Time | PPM | pH | Lapsed Time | PPM | pH |
|---|---|---|---|---|---|
| 0:45 | 36 | 7.45 | 0:45 | 20 | 7.53 |
| 1:30 | 45 | 7.29 | 1:30 | 41 | 7.35 |
| 2:30 | 44 | 7.30 | 2:30 | 44 | 7.30 |
| 3:30 | 44 | 7.32 | 3:30 | 41 | 7.32 |
|  |  |  | 4:30 | 41 | 7.34 |

|  | 1% Luwax | 1% C/S grnl |
|---|---|---|
| Start Temp (F.) | 81 | 82 |
| Start pH | 7.85 | 7.85 |
| Weight (gm) | 3.9 | 4 |
| Volume (liters) | 14 | 14 |
| Speed setting (1-5) | 1 | 1 |

| Lapsed Time | PPM | pH | Lapsed Time | PPM | pH |
|---|---|---|---|---|---|
| 0:45 | 30 | 7.57 | 0:45 | 15 | 7.48 |
| 1:30 | 47 | 7.05 | 1:30 | 32 | 7.30 |
| 2:30 | 49 | 7.04 | 2:30 | 35 | 7.32 |
| 3:30 | 47 | 7.07 | 3:30 | 32 | 7.35 |
|  |  |  | 4:30 | 31 | 7.39 |
|  |  |  | 5:30 | 34 | 7.43 |

-continued

TESTING Round 2:

|  | 1% C/S | Control |
|---|---|---|
| Start Temp (F.) | 84 | 82 |
| Start pH | 7.85 | 8.01 |
| Weight (gm) | 3.9 | 4.0 |
| Volume (liters) | 14 | 14 |
| Speed setting (1-5) | 1 | 1 |

| Lapsed Time | PPM | pH | Lapsed Time | PPM | pH |
|---|---|---|---|---|---|
|  |  |  | 0:00 | 0 | 8.01 |
|  |  |  | 0:45 | 18 | 7.64 |
| 0:45 | 32 | 7.22 | 1:30 | 36 | 7.43 |
| 1:30 | 60 | 7.23 | 2:30 | 35 | 7.43 |
| 2:30 | 61 | 7.27 | 3:30 | 33 | 7.44 |
| 3:30 | 60 | 7.31 | 4:30 | 32 | 7.45 |
| 4:30 | 59 | 7.34 | 5:30 | 29 | 7.47 |
|  |  |  | 6:30 | 30 | 7.50 |
|  |  |  | 7:30 | 29 | 7.52 |
|  |  |  | 8:30 | 26 | 7.54 |
|  |  |  | 9:30 | 24 | 7.57 |
|  |  |  | 10:30 | 23 | 7.59 |
|  |  |  | 11:30 | 23 | 7.61 |
|  |  |  | 12:30 | 23 | 7.63 |
|  |  |  | 13:30 | 20 | 7.66 |
|  |  |  | 14:30 | 19 | 7.69 |
|  |  |  | 15:30 | 18 | 7.71 |
|  |  |  | 16:30 | 17 | 7.73 |
|  |  |  | 29.3 | 8 | 7.99 |

| 1% Silicate | |
|---|---|
| Start Temp (F.) | 83 |
| Start pH | 7.85 |
| Weight (gm) | 4.0 |
| Volume (liters) | 14 |
| Speed setting (1-5) | 1 |

| Lapsed Time | PPM | pH |
|---|---|---|
| 0:45 | 25 | 7.58 |
| 1:30 | 37 | 7.40 |
| 2:30 | 33 | 7.41 |
| 3:30 | 32 | 7.44 |
| 4:30 | 31 | 7.47 |

This set of data illustrates that as the concentration of polymer increases in relation to the surface area of the reactant composition, the sustainability of the in-situ generated oxidant release increases. By incorporating a stiffening agent with the polymer, lower levels of polymer can be employed while dramatically increasing the Weight % Yield. In the case of adding 1 wt. % Carbopol®/Metasilicate mixture to the powdered reactants prior to agglomerating, the "weight % Yield" increased to over 21% of the total mass of tablet.

This synergistic effect is very useful in restricting the diffusion of the reactants, thereby sustaining a high concentration of reactants until the reactions are near completion without the need for additional coatings, binders, or containers. One benefit is the ability to formulate compositions using high concentrations of reactants without the need for including inert materials to provide porosity or heat to improve reaction kinetics. As a result of utilizing this invention, higher concentrations of reactants can be incorporated into the tablet, and a higher "weight % yield" is achieved than that obtained using prior art methods. The agglomerates produced are also self-sustaining, in that they do not require additional containers such as membranes, paper wrappings etc. to effectively function in an environment that induces rapid dilution of the reactants.

Figure 12A:
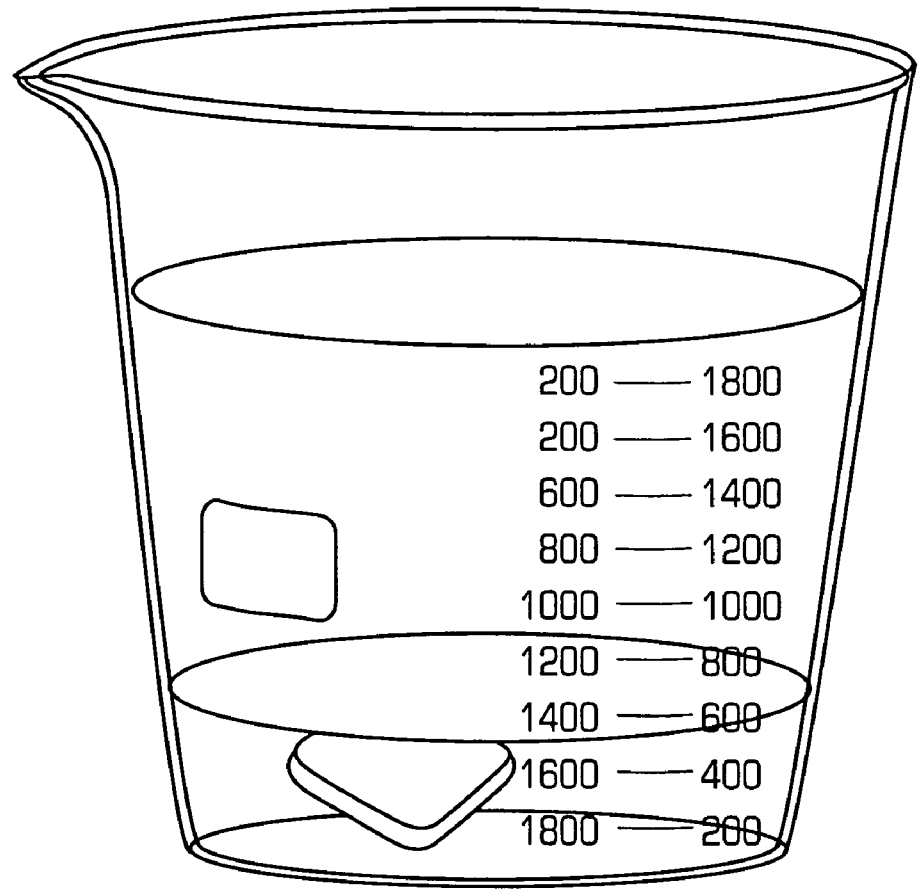
FIGS. 12A, 12B, and 12C illustrate how a gelatinous structure dissolves in the main solvent.

FIG. 12A shows a gelatinous structure 100 that is dropped into water. The gelatinous structure 100 in this case is a tablet weighing approximately 4 grams made of reactant powder (not granules as in FIG. 6) made from 30 wt. % dichloroisocyanuric acid, 30 wt. % sodium bisulfate, and 40 wt. % sodium chlorite admixed with a powder comprised of 60% Carbopol® 676 and 40% sodium metasilicate. The mixture was agglomerated in a die using pressure to form a tablet. The final composition of the agglomerated mixture has: 27 wt. % dichloroisocyanuric acid, 27 wt. % sodium bisulfate, 36 wt. % sodium chlorite, 6 wt. % Carbopol® 676, and 4 wt. % sodium metasilicate.

Figure 12B:
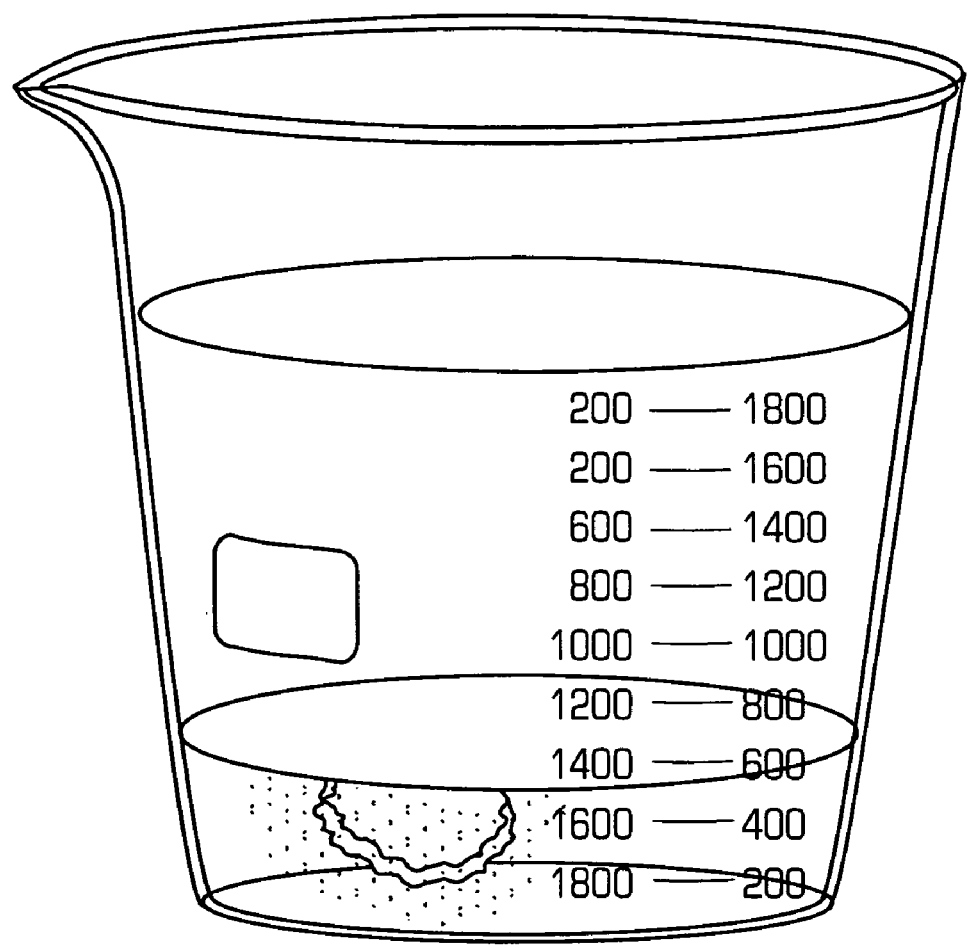

FIG. 12B shows the gelatinous structure 100 after it has been immersed in water for 52 minutes. At this point, the gelatinous structure 100 enclosed compartment containing the reactants is clearly visible.

Figure 12C:
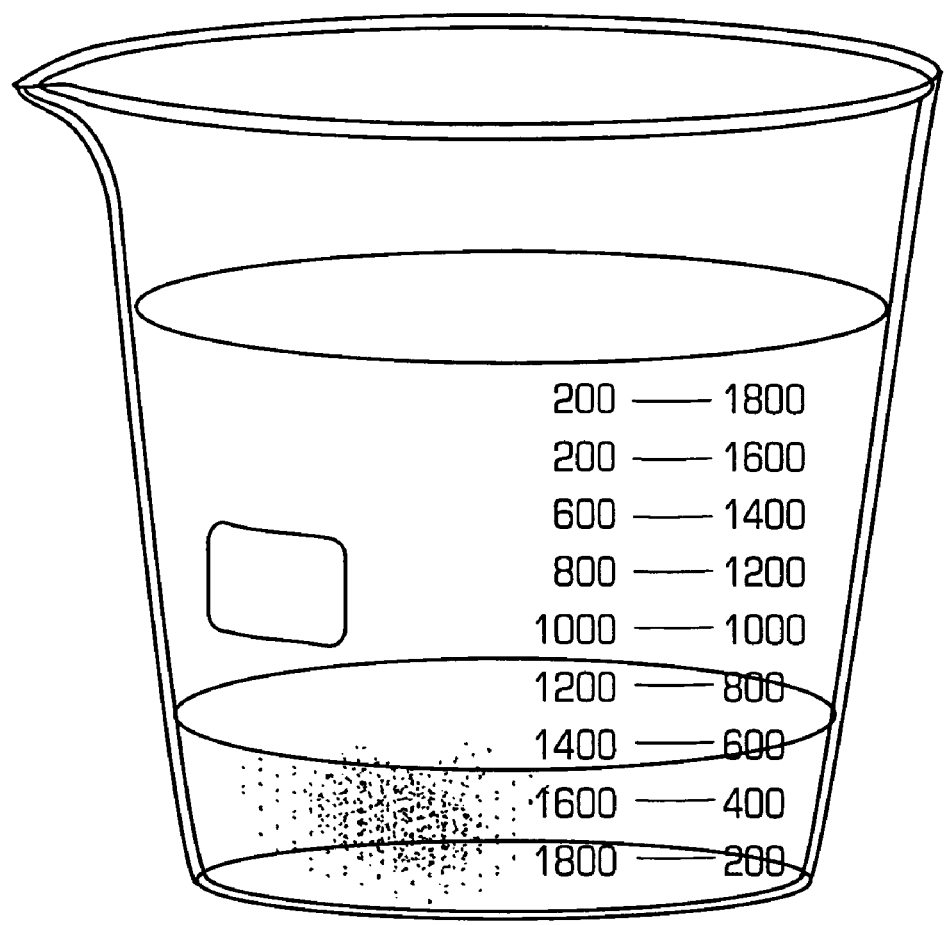

FIG. 12C shows the gelatinous structure 100 after it has been immersed in the water for 30 hours. At this point, the remainder of the reactant core is clearly visible within the chamber produced by the gelatinous structure.

Figure 13:
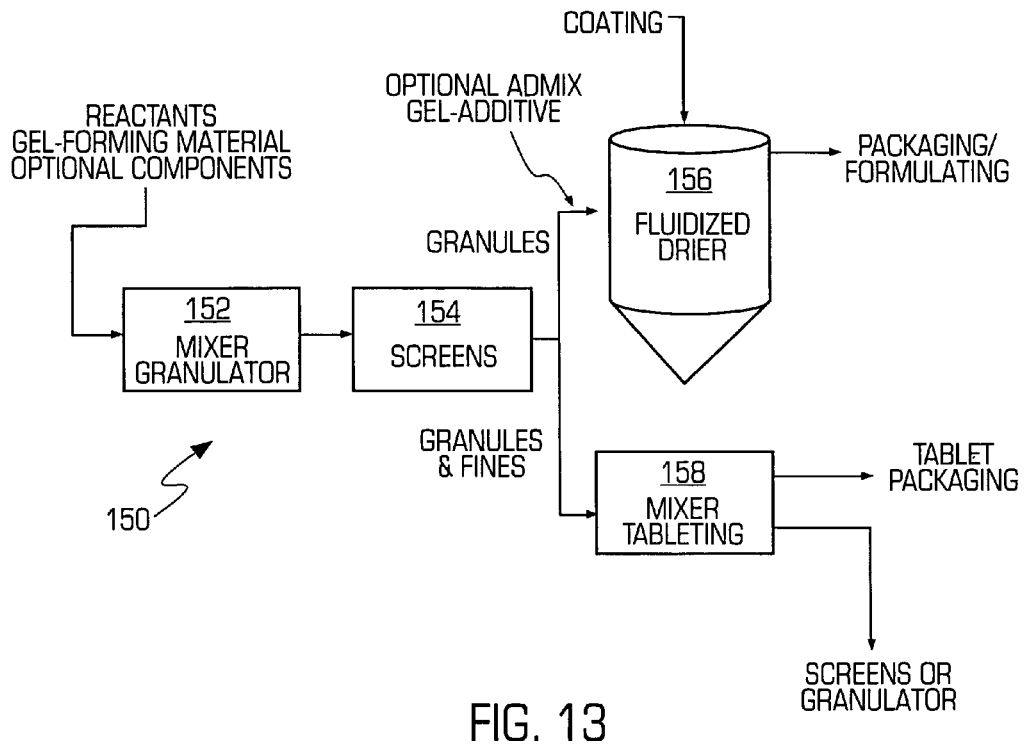
FIG. 13 illustrates a process for preparing the gelatinous structure.

FIG. 13 illustrates a process 150 for producing the gelatinous structure 100. Reactants and a gel-forming material are added into a mixer granulator 152 and put through screens 154. The granules that come out of the screens 154 are then sent to a fluidized drier 156, to which coating material (e.g., more gel-forming material, environmentally protective material) is added to coat the granules. The product of the fluidized drier 156, which looks like the coated granules of FIG. 7 or FIG. 9, may be sent to an agglomerator (not shown) to be agglomerated, function as self-sustaining granules, or formulated with other materials. After the agglomeration, the "cluster" will look like the embodiment of FIG. 6.

Alternatively, the granules and fines coming out of the screens 154 may be sent to a tableting mixer 158. The outcome of the tableting mixer 158 is the tablet of FIG. 8.

Figure 14:
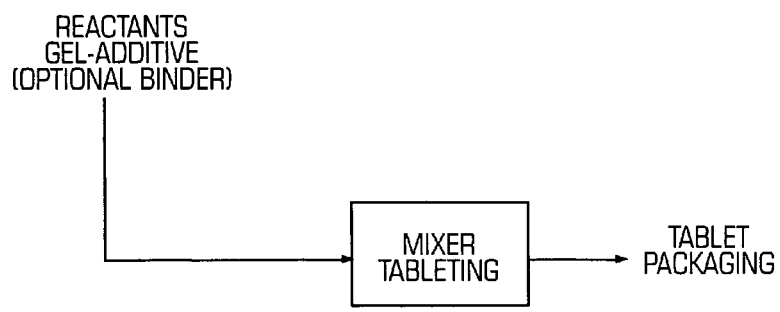
FIG. 14 illustrates a process where the reactants and gel-forming material are combined, mixed, and agglomerated to form a tablet.

FIG. 14 illustrates a process where the reactants and gel-forming material are combined, mixed, and agglomerated to form a tablet. A binder material may be added, optionally. The process of FIG. 14 is a simplified version of the process of FIG. 13 in that it does not include the mixer granulator 152 or the screens 154.

By first forming granules followed by agglomerating the granules, the "Weight % Yield" of in-situ generated oxidants is significantly improved over agglomerates produce from powders having the same chemical composition. By combining a gel-Forming material with the reactants, gelatinous chambers are formed in which, the reactants generate higher yields of product. When sufficient viscosity is obtained within the geleatinous structure that is formed, the agglomerate is self-sustaining, such that even while exposed to conditions sufficiently turbulent that the agglomerate does not rest on any surface, while being exposed to external pH conditions and dilutions that would inhibit generation of the oxidant, the weight % Yield is sustained. Furthermore, when the hydro-colloid forming polymer is added in sufficient quantities as to be effectively distributed in the reactant composition, a sustained release of oxidant is achieved. Further still, the wt % of hydro-colloid polymer can be reduced while obtaining the sustained release of oxidant by admixing the gel-forming material to granules prior to forming the tablet, versus admixing the gel-forming material to the powder. By reducing the surface area, it is believed the quantity of polymer required to induce formation of the chambers is significantly reduced. Also, the localized high concentrations of polymer induced by formation of distinct boundaries of polymer between the granules of reactants, increases the localized viscosity and rigidity of the gel-structure, thereby inducing the slow release of oxidant from the chambers. The same effect can be obtained as illustrated in the test results when higher quantities of polymer are added to the powder composition.

As a result of these findings, it is possible to produce agglomerates for a variety of in-situ generated oxidants that can produce high "Weight % Yield" of the desired oxidants independent of secondary coatings, housings, or containment. Further still, the data clearly illustrated that water-soluble compositions for in-situ generation of chlorine dioxide can be produced that provide an increase in "Weight % Yield" of 300% higher than water soluble agglomerate compositions disclosed in the prior art "404". Further still, the compositions of the disclosed invention increase the Weight % Yield of chlorine dioxide over any disclosed compositions of "404" even water-insoluble compositions, by as much 43%. The compositions of the invention can be designed to provide rapid release of of oxidant at higher yield, or maintain a sustained release of extended periods.

C. Biocidal Composition Using Synergistic Effect of Chlorine Dioxide and Halogen The biocide compositions of the invention includes a composition for the in-situ generation of an oxidizer and a free halogen donor. Although the examples herein focus on chlorine dioxide as an exemplary oxidizer, the synergistic effect may be achieved with oxidizers other than chlorine dioxide, such as the target products mentioned above.

There are many configurations that use gelling agents to generate the chlorine dioxide. For utility in applications such as industrial cooling tower treatment where the biocide tablets may be incorporated into an enclosed dispenser, the release rate of the chlorine dioxide may be controlled for optimization.

As described above, addition of a gel-forming material to high-solubility reactants such as dichloroisocyanuric acid, acid donors such as sodium bisulfate and other optional reactants that initiate reaction with chlorite to produce in-situ generated chlorine dioxide, dramatically increases the percent conversion of chlorite along with substantially increasing the weight % yield of the chlorine dioxide composition as a result of producing chambers having a gel-structure that restricts diffusion of the reactants into the solvent. It demonstrated above that a small 4-gram tablet could be made to sustain release of chlorine dioxide for over 30 hours, while untreated tablets of the same composition where completely dissolved in approximately 90 seconds. This same effect can be achieved with the high-solubility inorganic bromide salts to produce hypo-bromite containing solutions.

This capability not only increases the percent conversion and improves the weight % yield of the chlorine dioxide component of a composition, but also improves the safety of using such compositions by preventing rapid release of chlorine dioxide when feed systems fail or the tablets are exposed to a stagnant condition while immersed in water. Rapid or excessive release of chlorine dioxide could present significant hazards due to pressure buildup, explosion, and injury to personnel exposed to the vapors or catastrophic failure of the equipment. By combining the sustained release chlorine dioxide generating composition into a matrix of low-solubility free halogen donors, a safe and effective agglomerate results that provides biocidal efficacy better than the agents used alone.

The invention discloses various agglomerate biocidal compositions that provide multiple oxidizers which in turn provide a synergistic effect, and provide for the cost effective methods of producing the agglomerates. Another added benefit of the disclosed invention is that the appropriate composition can be selected based on the needs of the application. In highly stressed systems, a chlorine dioxide-bromine composition can be applied, whereas in lesser stressed systems, a chlorine dioxide-chlorine composition is suitable.

The agglomerates can be applied in the form of a granule or tablet of any convenient size and shape. Of significant advantage over conventional technologies is the ability to combine these oxidizers while achieving a high "weight % yield" of chlorine dioxide, and high % conversion of the chlorite without the addition of large quantities of inert salts and clays.

The compositions are comprised of granules capable of independently producing in-situ generated chlorine dioxide in high yield, as well as larger bodies comprised of a plurality of granules with additional halogen-based biocidal agents such as chlorine and/or bromine. Further still, an agglomerate comprised of several different layers or boundaries whereby the in-situ generating portion of the tablet is coated or layered between a free halogen donor, which may or may not include additional gel forming agent. In another form of the art, the bromine is also produced in-situ by reaction between chlorine donor and bromide ions alone with the chlorine dioxide, thereby maximizing chlorine dioxide and bromine generation, while releasing low levels of the less effective chlorine which is readily consumed in highly contaminated waters.

Tablets can be produced by combining trichloroisocyanuric acid and a chlorite donor. In another example, granules can be produced by combining dichloroisocyanuric acid, chlorite donor, and an acid source. The granules can be coated with a coating having a solubility substantially lower than that of the reactants, and/or incorporate a gel forming additive. These granules can be used independently as a biocidal agent, or admixed with additional halogen and formed into granules or tablets. In all examples, a gel-forming additive can be applied to further enhance the % conversion of chlorite to chlorine dioxide, as well as provide added safety for the practical use of the composition.

The compositions of the invention can be produced efficiently to provide a cost-effective and safe means of applying chlorine dioxide to recirculating water systems such as cooling water system, pools and spas. By combining oxidants as disclosed, effective biocidal performance can be achieved even in high demand applications where excess amount of bromine or continued regeneration of bromide ions is either not effective or economical. Combining a high yield chlorine dioxide technology with a bromine donor provides a synergistic effect, even when residual chlorine and/or bromine are converted to halogenated amine compounds. The elimination of expensive feed equipment and the difficulties in controlling and optimizing ratios are eliminated. Also, The compositions of the disclosed invention can be made to produce Class II oxidants as defined by the National Fire Protection Association so as to allow for increased storage and limited restrictions as pertaining to Department of Transportation regulations.

Also, due to the limited solubility of these compositions, the concentration of chlorine dioxide allowed to accumulate in a closed feed system will be limited based on the solubility characteristics of the specific composition. While it would be expected that due to the solubility of many of the disclosed reactants use to generate the chlorine dioxide, there exist a potential for higher concentrations of chlorine dioxide to accumulate in the system which loses flow of water and is allowed to sit stagnant in water. Addition of gel-forming agents such as Carbopol®, as well as a low solubility binding agents such as polyethylene wax (Luwax®), calcium stearate and the like, can dramatically slow the liberation of chlorine dioxide even without inclusion in the low solubility halogen matrix. As the solution reaches saturation, the rate of chlorine dioxide generation would taper off as to prevent excess pressure buildup inside the feeder from the continued or excessive generation of chlorine dioxide.

To further enhance the longevity of the chlorine dioxide in the circulating water, a non-ionic surfactant can be added to either the water or directly to the composition. A few examples of non-ionic surfactants include: polyoxyethylene alkyl ethers, polyoxyethylene alkylaryl ethers, polyethylene glycol fatty acid esters, and the like.

Chlorine Dioxide Versus Chlorine

The use of gaseous chlorine as a microbiocide for industrial cooling systems is declining because of safety, environmental and community impact considerations. Various alternatives have been explored, including bleach, bleach with bromide, bromo-chlorodimethyl hydantoin (BCDMH), non-oxidizing biocides, ozone, and chlorine dioxide, among others. Chlorine dioxide offers some unique advantages, due to its selectivity, effectiveness over a wide pH range, and speed of kill. Safety and cost issues have restricted its use as a viable replacement.

The following "report card" compares the effectiveness of chlorine dioxide with other oxidizing biocides, and illustrates the superior performance of chlorine dioxide as a biocide:

COMPARISON OF OXIDIZING BIOCIDES IN LIGHT
OF THE CRITERIA OF AN "IDEAL" BIOCIDE
Report Card

| | HOCl | HOBr | $ClO_2$ | $O_3$ |
|---|---|---|---|---|
| PERFORMANCE | | | | |
| High pH | C | B | A | A |
| Kinetics | B | B | A | A |
| Selectivity | C | B | A | D |
| Biofilm | B | B | A | C |
| System Contamination | C | C | A | D |
| Bacterial Recovery | B | B | A | C |
| ENVIRONMENTAL | | | | |
| THM | C | C | B | A |
| TOX | C | C | B | A |
| Toxicity | | | | |
| of primary oxidant | B | A | A | C |
| of oxidation by-products | B | B | C | A |
| of oxidation reaction products | B | C | A | D |
| residual life (short life best) | C | B | C | A |
| SAFETY | | | | |
| Easy to Use | B | B | C | B |
| Safe to Handle | B | B | C | B |
| ECONOMICS | | | | |
| Clean System | A | B | B | C |
| Contaminated System | C | C | A | C |
| Cumulative GPA | 2.6 | 2.8 | 3.3 | 2.7 |

Figure 15:
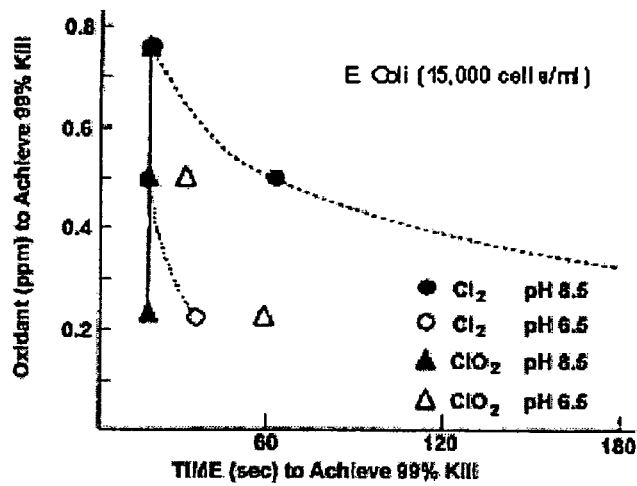
FIG. 15 is a graph comparing the biocidal effectiveness of chlorine and chlorine dioxide.

Many studies have been made comparing the disinfection efficiency of chlorine dioxide to chlorine. In one such study, varying dosages of chlorine dioxide or chlorine were added to solutions containing 15,000 viable cells/ml of *E. coli* at pH's of 6.5 and 8.5. The results are shown in FIG. 15. The abscissa is the time in seconds required to kill 99% of the viable bacterial cells. The ordinate is the initial dosage of oxidant.

FIG. 15 shows the decreasing effectiveness of chlorine as the pH increases, and the lack of a similar trend with chlorine dioxide. This is to be expected because chlorine resets with water rapidly to form hypochlorous and hydrochloric acids. Hypochlorous acid, the primary biocide, dissociates as a function of pH, forming the hypochlorite ion. Hypochlorite is reported to be from ½₀ to ⅟₃₀₀ as effective at microbiological control as hypochlorous acid.

Unlike chlorine, chlorine dioxide remains a true gas dissolved in solution. The lack of any significant reaction of chlorine dioxide with water is partly responsible for its retaining its biocidal effectiveness over a wide pH range. This property makes it a logical choice for cooling systems operated in the alkaline pH range, or cooling systems with poor pH control.

Figure 16:
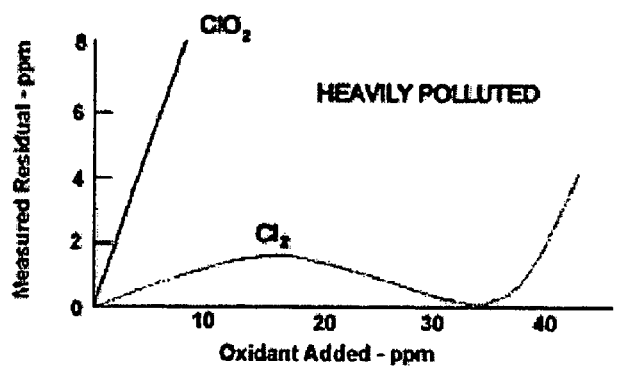
FIG. 16 shows the measured residual amounts of $ClO_2$ and $Cl_2$ for a highly polluted water stream.

Equivalent amounts of chlorine dioxide and chlorine were added to water streams with various levels of contamination. FIG. 16 shows the measured residual amounts of $ClO_2$ and $Cl_2$ for a highly polluted water stream. Residuals were measured after 30 minutes of contact, and the results were plotted against the initial dosage. The chlorine was largely consumed, regardless of how much was added. Chlorine dioxide, after some initial consumption, remained mostly unreacted. This characteristic is indicative of the much greater selectivity of chlorine dioxide than chlorine.

The disinfection requirements of an open recirculating industrial cooling system are markedly different from those of a potable water treatment facility. The disinfection goal of potable water facilities is the sterilization of water as measured by specific water borne pathogens. The goal of disinfection for industrial cooling systems is the removal or minimization of any biofilm, which retards heat transfer, causes biofouling, provides a place of agglomeration for marginally soluble or insoluble salts, and provides a place which nurtures and promotes the growth of highly corrosive anaerobic bacteria.

Figure 17:
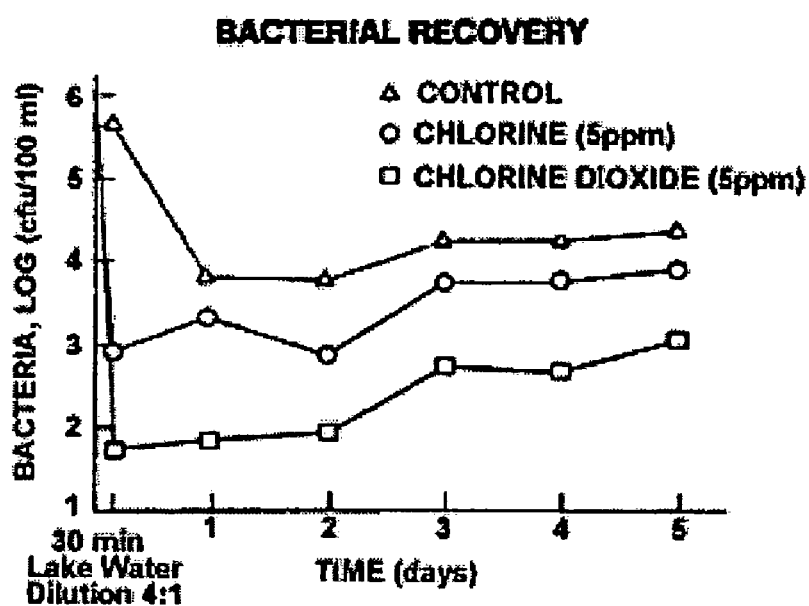
FIG. 17 shows the recovery of bacterial activity after a shock dosage with $ClO_2$ and $Cl_2$.

FIG. 17 shows the recovery of bacterial activity after a shock dosage with $ClO_2$ and $Cl_2$. One possible reason for the relatively slow re-growth of bacteria after sterilization by chlorine dioxide (FIG. 17) lies in its superior ability to penetrate and disperse a biomass. By effectively killing and stripping off any biofilm, bacteria are much slower to re-establish than when the biofilm is left intact.

Many researchers have cited the excellent biofilm removing properties of chlorine dioxide. In at least one previously reported case history, the introduction of chlorine dioxide into a heavily fouled cooling system resulted in an increase in both turbidity and calcium. These were explained by a dispersing of the biofilm which both increased turbidity and released small calcium carbonate particulates which had been trapped in the biofilm.

Other industries have made use of the excellent biofilm removal properties of chlorine dioxide, particularly the food industry. Small cooling towers, frequently contaminated by food products or by-products, have tremendous slime forming potential. Chlorine dioxide has achieved widespread usage in such systems, due to its excellent biofilm dispersing/bacterial disinfecting properties.

Chlorine Dioxide Combined with a Halogen

U.S. Pat. No. 5,464,636 (the '636 Patent) discloses a means of reducing the concentration of bromide donor in a recirculating system by optimizing the ratio of hypochlorite to bromide ions to induce re-activation of the bromide in the recirculating water thereby improving cost effectiveness of the bromine treatment. The '636 Patent demonstrates a means of optimizing the cost-effectiveness of using bromine-based biocides by re-activating the bromide in the recirculating water. However, the '636 Patent fails to describe the synergistic effects of combining chlorine dioxide with bromine based biocide. Also, in highly stressed systems where bromine is more effective than chlorine (such as systems contaminated with ammonia, hydrocarbons and the like), residual chlorine is readily consumed to produce chloramines and trihalomethanes which in effect inactivate the chlorine. The composition disclosed in the '636 Patent is therefore only economical as a regenerative bromine treatment application in a system experiencing low chlorine demand, in which case the added expense of bromine is unwarranted. This is illustrated in the following comparison of oxidizing biocides:

| System Type | pH | Effectiveness of Biocides |
|---|---|---|
| Clean | 6.8-8.0 | $Cl_2$ < NaOCl < HOCl + NaBr < $ClO_2$ < BCDMH < ozone |
|  | 8.0-9.3 | HOCl + NaBr < $ClO_2$ < BCDMH < $Cl_2$ < NaOCl < ozone |
| High Organic Load | 6.8-9.3 | $ClO_2$ < HOCl + NaBr < BCDMH < $Cl_2$ < NaOCl < ozone |
| Ammonia Contamination | 6.8-9.3 | $ClO_2$ < HOCl + NaBr < BCDMH < $Cl_2$ < NaOCl < ozone |

[values obtained from G. D. Simpson, et al., "A Focus on Chlorine Dioxide: The "Ideal" Biocide," Unichem International, Inc.]

Hypobromous acid also dissociates with pH. The dissociation curve is essentially equivalent to that of chlorine. Its curve is offset by about 1 pH unit toward the alkaline range from that of hypochlorous acid. For example, the pH of 50% dissociation of the hypohalous acid to the hypohalite anion is about 7.5 and 8.7 for chlorine and bromine, respectively.

Bromine reacts with amines and ammonia. Unlike chlorine, bromamines largely retain their biocidal effectiveness, being almost as effective as hypobromous acid. In addition, the bromamines formed have relatively short half-lives, thus eliminating the need for dechlorination in some plants.

Bromine has been shown to be significantly better than chlorine with regard to biofilm control, while others have found there to be little difference between chlorine and bromine.

TABLE 1

*C. parvum* Inactivation Using Chlorine Dioxide Followed by Free Chlorine

| Disinfectant | Level of Inactivation (log-units) | | |
|---|---|---|---|
| | pH 6.0 | pH 8.0 | pH 11.0 |
| Chlorine dioxide | 1.0 | 1.4 | 1.6 |
| Free chlorine | 0 | 0 | 0 |
| Chlorine dioxide followed by free chlorine | 2.2 | 3.0 | 2.3 |
| Inactivation attributed to synergism | 1.2 | 1.6 | 0.7 |

Source: Finch, 1997.
Chlorine dioxide 1.3 mg/L for 120 minutes, free chlorine 2.0 mg/L for 120 minutes.

TABLE 2

*G. muris* Inactivation Using Chlorine Dioxide Followed by Free Chlorine

| Disinfectant | Level of Inactivation (log-units) | |
|---|---|---|
| | pH 6.0 | pH 8.0 |
| Chlorine dioxide | 0.8 | 0.8 |
| Free chlorine | 0.8 | 0.6 |
| Chlorine dioxide followed by free chlorine | 2.2 | 2.0 |
| Inactivation attributed to synergism | 0.6 | 0.6 |

Source: Finch, 1997.
Chlorine dioxide: 1.0 mg/L for 10 minutes, free chlorine 2.0 mg/L for 30 minutes.

TABLE 3

*C. parvum* Inactivation Using Chlorine Dioxide Followed by Chloramine

| Disinfectant | Level of Inactivation (log-units) | | |
|---|---|---|---|
| | pH 6.0 | pH 8.0 | pH 11.0 |
| Chlorine dioxide | 1.0 | 1.5 | 1.6 |
| Monochloramine | 0 | 0 | 0 |
| Chlorine dioxide followed by monochloramine | 2.2 | 2.8 | 2.1 |
| Inactivation attributed to synergism | 1.2 | 1.3 | 0.5 |

Source: Finch, 1997.
Chlorine dioxide: pH 6, 8, and 11: 1.3 mg/L for 120 minutes.
Monochloramine: pH 6 and 11: 2.0 mg/L for 120 minutes, pH 8: 2.8 mg/L for 180 minutes.

Tables 1, 2, and 3 illustrate the synergistic effect of combining chlorine dioxide with free chlorine as well as byproducts of chlorine oxidation, i.e. chloramines. The combined effect dramatically increases the inactivation rate of a variety of organisms.

The synergistic effect may be achieved by using any bromine derivative (e.g., $Br_2$, HOBr, $OBr^-$) or chlorine derivative (e.g., $Cl_2$, HOCl, $OCl^-$).

An environmentally protective coating may be formed around the binder layer to prevent the agglomerate composition from premature reaction or decomposition prior to carrying out the function of a reactor.

FIGS. 18A, 18B, 18C, 19A, 19B, and 19C illustrate different embodiments of the synergy-based oxidizing composition of the invention. In these embodiments, gel forming additives can be incorporated into either the reactant core components, the free halogen donor, or both. As described above, the reactants may be in the form of an agglomerate or granule(s).

Figure 18A:
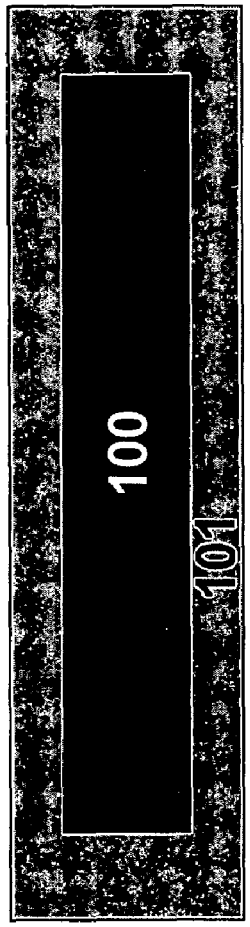
FIGS. 18A, 18B, and 18C illustrate an embodiment of the composition whereby a reactant core is surrounded by a coating containing at least one free halogen donor.
Figure 18B:
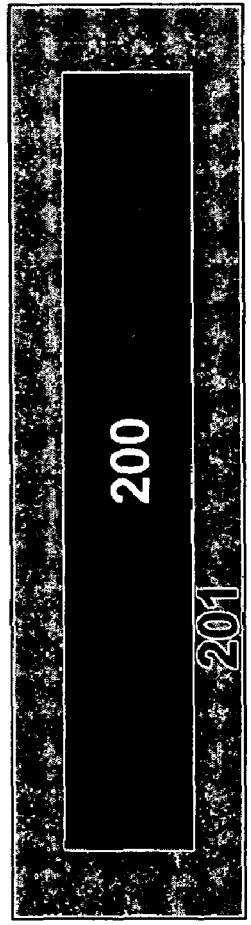
Figure 18C:
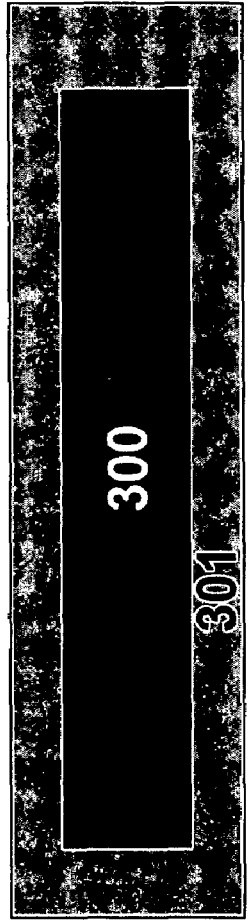

FIGS. 18A, 18B, and 18C demonstrate embodiments where the core is encapsulated by a layer of coating. In FIG. 18A, a core 100 of reactants is encapsulated by a coating 101 that contains the gel-forming material and the halogen. In FIG. 18B, a core 200 that contains reactants and gel-forming material is encapsulated by a coating 201 of halogen. In FIG. 18C, a core 300 that contains reactants and gel-forming material is encapsulated by a coating 301 that contains halogen and the gel-forming material. FIG. 18C demonstrates that the gel-forming material can be present in both layers.

Figure 19A:
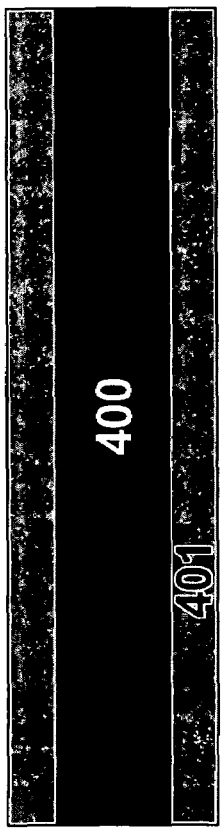
FIGS. 19A, 19B, and 19C illustrate an embodiment of the composition whereby a reactant layer is sandwiched between two layers of at least one free halogen donor.
Figure 19B:
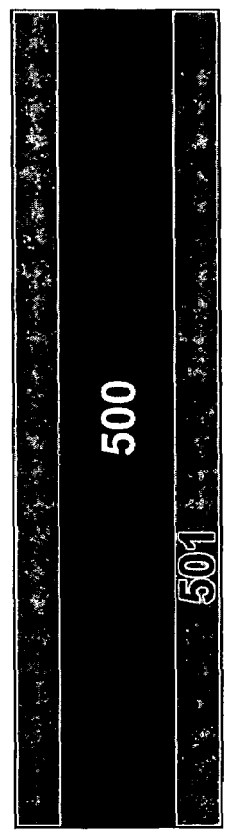
Figure 19C:
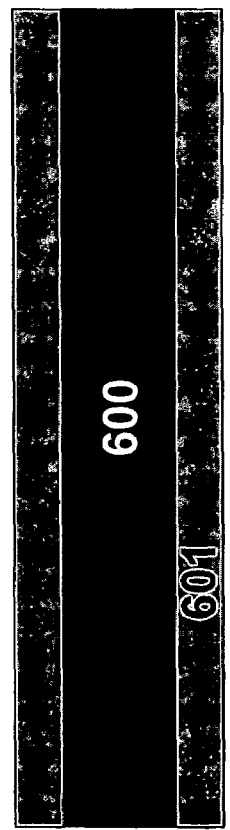

FIGS. 19A, 19B, and 19C demonstrate embodiments where a core layer is sandwiched between two outer coating layers. In FIG. 19A, a core 400 containing reactants is sandwiched between coating layers 401, each of which contains the gel-forming material and the halogen. In FIG. 19B, a core 500 of reactants and the gel-forming material is sandwiched between coating layers 501, which are effectively halogen layers. In FIG. 19C, a core 300 that contains reactants and the gel-forming material is sandwiched between coating layers 601 that contain the halogen and the gel-forming material. To produce these embodiments, one of the coating layers containing free halogen donor is added to a die and leveled. The ingredients for the core are admixed and added to the leveled coating layer, and leveled. A top layer containing the free halogen donor is added and leveled, then all three layers are pressed.

Although not illustrated, each of the embodiments shown may be adapted to versions with more layers. For example, a reactant core tablet may be produced, a gel forming additive may be coated onto the reactant core tablet to form a first coating layer, followed by a second coating comprised of the free halogen donor. If desired, different types of halogen (e.g., chlorine and bromine) may be incorporated into a composition.

The tablets illustrated in FIGS. 18A, 18B, and 18C and FIGS. 19A, 19B, and 19C can be commercially produced using multi-layer tableting equipment such as a "Hata three-layer tableting press" sold by Elizabeth-Hata International, 14559 Route 30, 101 Peterson Drive, North Huntingdon, Pa. However, a Carver press can also be used for laboratory scale productions using established tableting techniques. The tablet of FIG. 15, is produced by first producing the reactant core which generated the in-situ oxidant, followed by removal of the tablet, and placement into a second-larger die that has been pre-coated with a free halogen donor. Additional halogen donor is added on top of the core tablet, leveled, then pressed to form a coated core.

The composition of the invention is effective as a biocide and algaecide treatment for use in recirculated water systems. While the foregoing has been with reference to a particular embodiment of the invention, it will be appreciated by those skilled in the art that changes in this embodiment may be made without departing from the principles and spirit of the invention.

What is claimed is:

1. A water-soluble composition that generates chlorine dioxide with a yield of at least 14 weight % and a chlorite conversion to chlorine dioxide of at least 70 weight %, and releases a biocidal solution containing chlorine dioxide and free halogen, wherein the composition comprises:
   reactants capable of in-situ generating chlorine dioxide through a chemical reaction when contacted by a main solvent, the reactants including a free halogen donor, an acid source different from the free halogen donor and a chlorite donor, wherein the chlorite donor is about 9-50 weight % of the composition, the acid source is about 10-80 weight % of the composition and the free halogen donor is from about 0.5 to 40 weight % of the composition;
   wherein said free halogen donor encapsulates and at least said chlorite donor; and
   a gel-forming material in contact with the reactants, wherein the gel-forming material makes up about 0.1 to 10 weight % of the composition and upon being exposed to the main solvent, forms a gelatinous structure that creates a chamber within the composition enclosing the reactants such that the chlorine dioxide is generated in the chamber, wherein the gelatinous structure restricts diffusion of the reactants and the chlorine dioxide out of the chamber, restricts the diffusion of the main solvent into the chamber, and wherein the gelatinous structure dissipates when a depletion level is reached inside the chamber;
   wherein different parts of the composition are exposed to the main solvent at different times.

2. The composition of claim 1, wherein the free halogen donor is at least one of a chlorinated isocyanuric acid, chlorinated hydantoin, and brominated hydantoin.

3. The composition of claim 1, wherein the free halogen donor comprises bromine.

4. The composition of claim 1, wherein the free halogen comprises chlorine.

5. The composition of claim 1, wherein the biocidal solution contains chlorine dioxide, at least one free bromine derivative, and at least one free chlorine derivative.

6. The composition of claim 1, wherein the reactants for generating the target product are in the form of an agglomerate.

7. The composition of claim 6, wherein the agglomerate is in the form of a tablet.

8. The composition of claim 6, wherein the agglomerate contains the gel-forming material inside said agglomerate.

9. The composition of claim 1, wherein the reactants are coated with the gel-forming material.

10. The composition of claim 9, wherein the gel-forming material encapsulates the reactants by forming a coating.

11. The composition of claim 9, wherein the gel-forming material forms a membrane upon contacting the main solvent.

12. The composition of claim 1, wherein the biocidal solution provides virucidal, fungicidal, and algicidal effect.

13. The composition of claim 1 further comprising a solubility-reducing additive.

14. The composition of claim 13, wherein the solubility-reducing additive comprises a substantially water-insoluble hydrocarbon-based wax.

15. The composition of claim 13, wherein the solubility-reducing additive is a mineral salt of carboxylic acid having at least 16 carbons.

16. The composition of claim 13 further comprising a non-ionic surfactant that stabilizes chlorine dioxide in a recirculating body of the main solvent.

17. The composition of claim 1, wherein the free halogen donor comprises one or more of: chlorinated isocyanuric acid, trichloroisocyanuric acid (TCCA), and dicloroisocyanuric acid, brominated hydantoin, dibromodiniethylhydantoin, bromochlorodimethyl hydantoin, and chlorinated hydantoin.

18. The composition of claim 1, wherein the acid source comprises potassium monopersulfate.

19. The composition of claim 1, wherein the acid source comprises sodium bisulfate.

20. A water-soluble composition that generates chlorine dioxide with a yield of at least 14 weight % and a chlorite conversion to chlorine dioxide of at least 70 weight %, and releases a biocidal solution containing chlorine dioxide and free halogen, wherein the composition comprises:
   reactants capable of in-situ generating chlorine dioxide through a chemical reaction when contacted by a main solvent, the reactants including a free halogen donor, an acid source different from the free halogen donor and a chlorite donor, wherein the chlorite donor is about 9-50 weight % of the composition, the acid source is about 10-80 weight % of the composition and the free halogen donor is from about 0.5 to 40 weight % of the composition;
   wherein said free halogen donor sandwiches at least said chlorite donor and a gel-forming material in contact with the reactants, wherein the gel-forming material makes up about 0.1 to 10 weight % of the composition and upon being exposed to the main solvent, forms a gelatinous structure that creates a chamber within the composition enclosing the reactants such that the chlorine dioxide is generated in the chamber, wherein the gelatinous structure restricts diffusion of the reactants and the chlorine dioxide out of the chamber, restricts the diffusion of the main solvent into the chamber, and wherein the gelatinous structure dissipates when a depletion level is reached inside the chamber;

wherein different parts of the composition are exposed to the main solvent at different times.

21. The composition of claim 20, wherein the free halogen donor is at least one of a chlorinated isocyanuric acid, chlorinated hydantoin, and brominated hydantoin.

22. The composition of claim 20, wherein the free halogen comprises bromine.

23. The composition of claim 20, wherein the biocidal solution contains chlorine dioxide and at least one free bromine derivative.

24. The composition of claim 20, wherein the free halogen comprises chlorine.

25. The composition of claim 20, wherein the biocidal solution contains chlorine dioxide, at least one free bromine derivative, and at least one free chlorine derivative.

26. The composition of claim 20, wherein the reactants for generating the target product are in the form of an agglomerate.

27. The composition of claim 26, wherein the agglomerate contains the gel-forming material inside said agglomerate.

28. The composition of claim 26, wherein the reactants are coated with the gel-forming material.

29. The composition of claim 28, wherein the gel-forming material encapsulates the reactants by forming a coating.

30. The composition of claim 29, wherein the gel-forming material forms a membrane upon contacting the main solvent.

31. The composition of claim 20, wherein the biocidal solution provides virucidal, fungicidal, and algicidal effect.

32. The composition of claim 20, further comprising a non-ionic surfactant that stabilizes chlorine dioxide in the main solvent.

33. The composition of claim 20, wherein the free halogen donor comprises one or more of: chlorinated isocyanunc acid, trichloroisocyanuric acid (TCCA), and dicloroisocyanuric acid, brominated hydantoin, dibromodimethylhydantoin, bromochlorodimethyl hydantoin, and chlorinated hydantoin.

34. The composition of claim 1, wherein the acid source comprises potassium monopersulfate.

35. The composition of claim 1, wherein the acid source comprises sodium bisulfate.

* * * * *